(12) United States Patent
Prerau et al.

(10) Patent No.: US 11,540,769 B2
(45) Date of Patent: *Jan. 3, 2023

(54) SYSTEM AND METHOD FOR TRACKING SLEEP DYNAMICS USING BEHAVIORAL AND PHYSIOLOGICAL INFORMATION

(71) Applicant: THE GENERAL HOSPITAL CORPORATION, Boston, MA (US)

(72) Inventors: Michael J. Prerau, Watertown, MA (US); Patrick L. Purdon, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 806 days.

This patent is subject to a terminal disclaimer.

(21) Appl. No.: 15/305,596

(22) PCT Filed: Apr. 28, 2015

(86) PCT No.: PCT/US2015/028039
§ 371 (c)(1),
(2) Date: Oct. 20, 2016

(87) PCT Pub. No.: WO2015/168151
PCT Pub. Date: Nov. 5, 2015

(65) Prior Publication Data
US 2017/0035351 A1    Feb. 9, 2017

Related U.S. Application Data

(60) Provisional application No. 61/985,180, filed on Apr. 28, 2014.

(51) Int. Cl.
*A61B 5/00*    (2006.01)
*A61B 5/08*    (2006.01)
(Continued)

(52) U.S. Cl.
CPC ........ *A61B 5/4812* (2013.01); *A61B 5/02055* (2013.01); *A61B 5/08* (2013.01);
(Continued)

(58) Field of Classification Search
CPC .... A61B 5/4809; A61B 5/4812; A61B 5/4815
(Continued)

(56) References Cited

U.S. PATENT DOCUMENTS 7,593,767 B1 * 9/2009 Modarres ............. A61B 5/4818
600/544
2001/0031930 A1 * 10/2001 Roizen ..................... A61B 5/18
600/545

(Continued)

FOREIGN PATENT DOCUMENTS

DE    102004010398 A1 * 9/2005    ............... A61B 5/00
WO    WO-0040148 A1 * 7/2000    ............. A61B 5/048

OTHER PUBLICATIONS

"Tracking the Sleep Onset Process: An Empirical Model of Behavioral and Physiological Dynamics" by Prerau et al. Published on Oct. 2, 2014 in PLOS journal of computational biology.*
(Continued)

*Primary Examiner* — Jonathan T Kuo
*Assistant Examiner* — Zahed Kabir
(74) *Attorney, Agent, or Firm* — Quarles & Brady LLP

(57) ABSTRACT

A system and method is provided for tracking sleep dynamics in a subject. In one aspect, a method includes acquiring physiological data using sensors positioned about the subject, and acquiring behavioral data using input provided by the subject. The method also includes generating a statistical model of wakefulness by combining information obtained from the acquired physiological data and behavior data, and estimating a probability indicative of a degree to which the subject is awake at each point in time during sleep onset
(Continued)

using the statistical model. The method further includes generating a report indicative of sleep onset in the subject.

27 Claims, 32 Drawing Sheets

(51) Int. Cl.
| | |
|---|---|
| *G16H 40/63* | (2018.01) |
| *G16H 50/30* | (2018.01) |
| *G16H 50/50* | (2018.01) |
| *A61B 5/0205* | (2006.01) |
| *G06K 9/00* | (2022.01) |
| *A61B 5/369* | (2021.01) |
| *A61B 5/389* | (2021.01) |
| *G06V 40/20* | (2022.01) |
| *A61B 5/0533* | (2021.01) |
| *A61B 5/145* | (2006.01) |
| *A61B 5/021* | (2006.01) |
| *A61B 5/11* | (2006.01) |
| *A61B 5/318* | (2021.01) |
| *A61B 5/374* | (2021.01) |
| *A61B 5/398* | (2021.01) |
| *A61B 3/113* | (2006.01) |

(52) U.S. Cl.
CPC .............. *A61B 5/369* (2021.01); *A61B 5/389* (2021.01); *A61B 5/4848* (2013.01); *A61B 5/681* (2013.01); *A61B 5/6825* (2013.01); *A61B 5/6898* (2013.01); *A61B 5/7246* (2013.01); *G06K 9/00536* (2013.01); *G06V 40/20* (2022.01); *G16H 40/63* (2018.01); *G16H 50/30* (2018.01); *G16H 50/50* (2018.01); *A61B 3/113* (2013.01); *A61B 5/021* (2013.01); *A61B 5/0533* (2013.01); *A61B 5/0816* (2013.01); *A61B 5/11* (2013.01); *A61B 5/1118* (2013.01); *A61B 5/14542* (2013.01); *A61B 5/318* (2021.01); *A61B 5/374* (2021.01); *A61B 5/398* (2021.01); *A61B 5/7264* (2013.01)

(58) Field of Classification Search
USPC ........................................................ 600/301
See application file for complete search history.

(56) References Cited

U.S. PATENT DOCUMENTS

| | | | |
|---|---|---|---|
| 2002/0193839 | A1* | 12/2002 | Cho .................... A61N 1/36521 607/11 |
| 2007/0276278 | A1* | 11/2007 | Coyle .................. A61B 5/0476 600/529 |
| 2009/0292180 | A1 | 11/2009 | Mirow |
| 2010/0081889 | A1 | 4/2010 | Downs, III et al. |
| 2010/0292545 | A1* | 11/2010 | Berka .................... A61B 5/048 600/301 |
| 2011/0018720 | A1 | 1/2011 | Rai et al. |
| 2011/0028418 | A1 | 2/2011 | Parker et al. |
| 2011/0230790 | A1 | 9/2011 | Kozlov |
| 2011/0301487 | A1* | 12/2011 | Abeyratne ............. G16H 50/50 600/544 |
| 2011/0306850 | A1 | 12/2011 | Hatlestad et al. |
| 2012/0022340 | A1* | 1/2012 | Heruth ................. A61B 5/0205 600/301 |
| 2012/0132202 | A1* | 5/2012 | Burton ................. A61B 5/4818 128/203.14 |
| 2012/0191425 | A1* | 7/2012 | Mott ....................... A61B 5/16 703/2 |
| 2015/0088024 | A1* | 3/2015 | Sackellares .......... A61B 5/0476 600/544 |

OTHER PUBLICATIONS

PCT International Search Report and Written Opinion, PCT/US2015/28039, dated Jul. 10, 2015, 12 pages.
PCT International Search Report and Written Opinion, PCT/US2015/28049, dated Aug. 4, 2015, 12 pages.

* cited by examiner

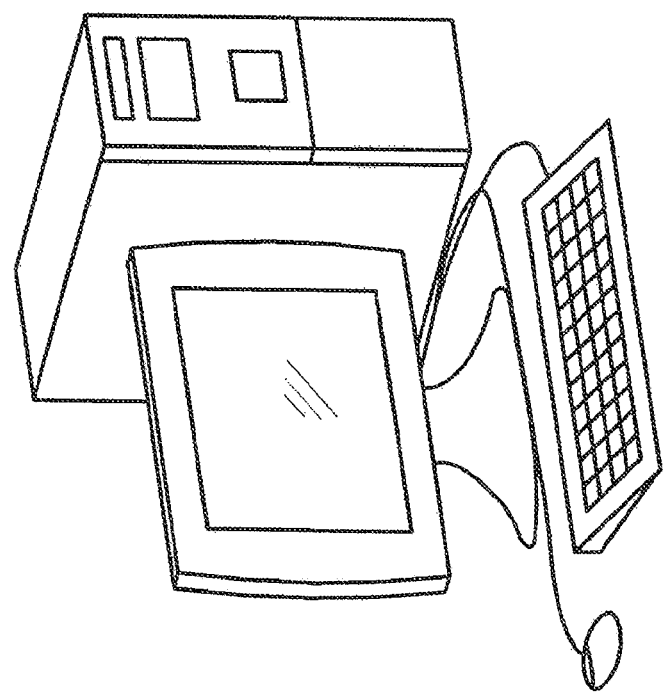
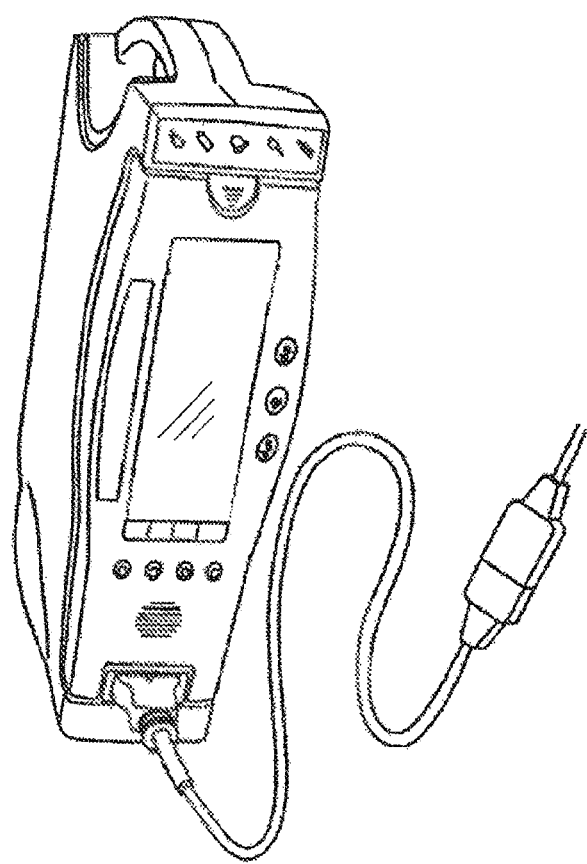
FIG. 1C

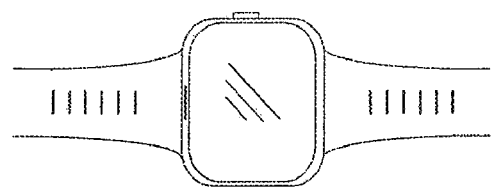
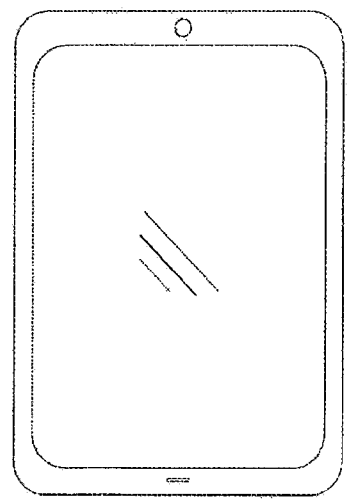
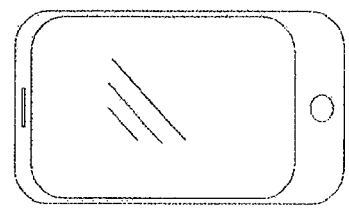
FIG. 1D

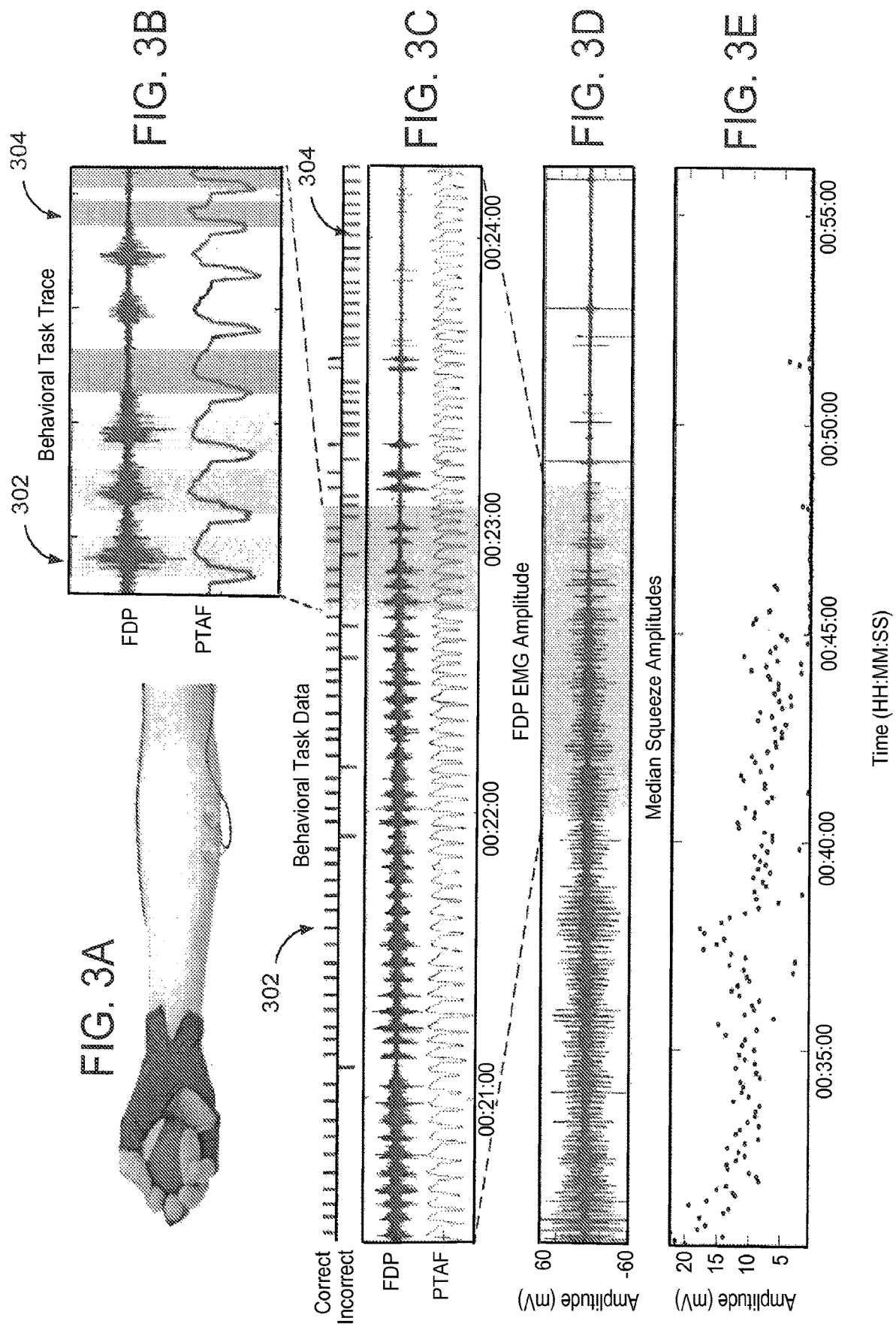

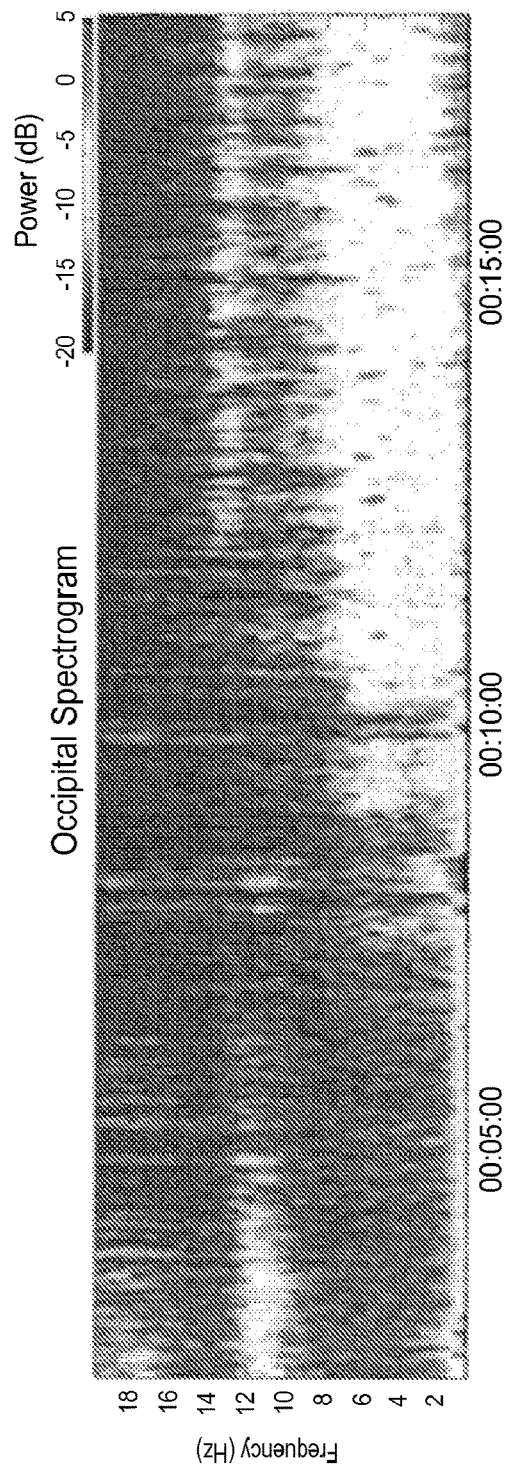
FIG. 8A
FIG. 8B

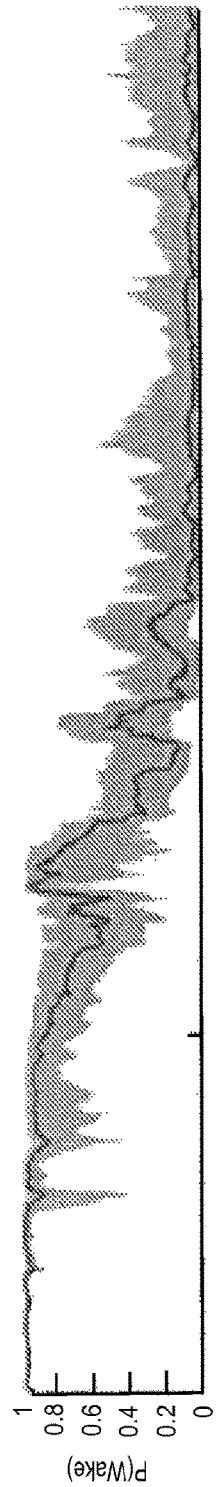
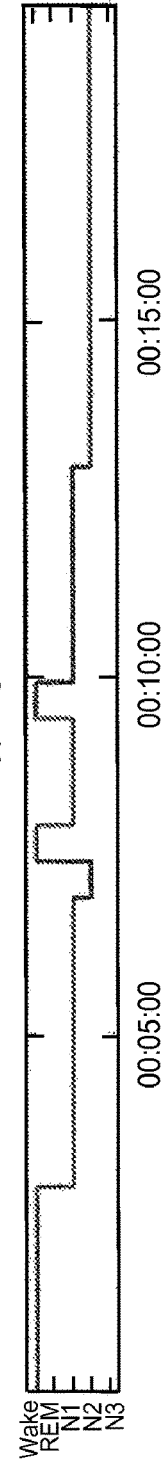

SYSTEM AND METHOD FOR TRACKING SLEEP DYNAMICS USING BEHAVIORAL AND PHYSIOLOGICAL INFORMATION

CROSS-REFERENCE TO RELATED APPLICATIONS

This application represents the U.S. National Stage of International Application No. PCT/US2015/028039, filed on Apr. 28, 2015 which claims the benefit of U.S. Provisional Patent Application Ser. No. 61/985,180, filed on Apr. 28, 2014, both of which are incorporated herein by reference for all purposes.

STATEMENT REGARDING FEDERALLY SPONSORED RESEARCH

This invention was made with government support under DP2-OD006465 awarded by National Institutes of Health. The government has certain rights in the invention.

BACKGROUND OF THE INVENTION

The field of the invention is related to systems and methods for monitoring conditions of a subject. More particularly, the invention is directed to systems and methods for tracking sleep and arousal using behavioral and physiological measurements.

Sleep is neural process consisting of multiple local and spatiotemporally-evolving factors, and direct observation of brain activity has been the primary means of tracking the onset of sleep. Generally, analysis of sleep has been performed through characterization of electroencephalogram ("EEG") recordings. For instance, some of the most evident changes observed during the sleep onset process ("SOP") include a progressive decrease in alpha (8-12 Hz) power, and a progressive increase in slow (<1 Hz), delta (0.5-5 Hz), and theta (5-8 Hz) power. Sleep is also associated with the occurrence of spindles, which are bursts of oscillatory brain activity. Such EEG measurements can provide information about the complex interplay between cortical and subcortical networks involved in the SOP. For instance, recent intracranial recording studies suggested that changes in thalamic activity occur prior to changes cortical activity, the timing of which can vary appreciably between subjects.

Current clinical practice for evaluating sleep includes visually scoring EEG recordings using the Rechtschaffen and Kales (R&K) system. In this system, the awake stage is differentiated from rapid eye movement ("REM") and non-rapid eye movement ("NREM") 1-3 stages of sleep, defined over 30-second epochs. This provides a manageable abstraction and discretization of the spatiotemporally dynamic continuum of EEG activity observed during the sleep, which allows an onset of sleep can be identified.

The R&K system, and other scoring systems employed before it, however, were found to have too coarse of a granularity to properly track SOP dynamics. To overcome this drawback, some researchers developed alternative scoring systems that include finer resolution. For instance, one group characterized multiple physiological appearances of drowsiness in the EEG. Another proposed 9 stages between wake and the first spindle, defined using 5-second epochs. Unfortunately, none of the above approaches have enjoyed wide implementation, perhaps due to a combination of labor-intensive scoring rules. In addition, such frameworks does not explicitly account for the diversity of normal variants, such as the absence of alpha EEG power during wakefulness in about 10% of the population. Moreover, they do not take into consideration individual variability associated with age, medications, or neurological disorders, and so forth.

Despite overwhelming evidence of its dynamic nature, the SOP is still most commonly viewed as a single instantaneous transition from being awake to being asleep based on a manual scoring criterion. This is readily apparent from semantics prevalent in the sleep literature, which refer to a "moment of sleep onset", or "sleep latency." Sleep onset is also defined by the American Academy of Sleep Medicine as the first appearance of any 30-second epoch that contains at least 15 seconds of sleep. In addition, such scoring guidelines reduce all degrees of wakefulness into a unitary stage, or "Wake" stage. Furthermore, current metrics of sleep onset are typically based either exclusively on behavior or exclusively on EEG recordings. As a result, behavioral and EEG methods have been shown to disagree as to precise point of sleep onset.

Understanding and quantifying the dynamic transition from wakefulness to sleep is of fundamental importance for sleep medicine and basic neuroscience alike. For instance, in sleep disorders such as insomnia, which has been associated with increased morbidity and mortality, the time course of the wake/sleep transition may be pathologically protracted, resulting in difficulty falling asleep. In disorders of excessive sleepiness (e.g., narcolepsy) or sleep deprivation, the wake/sleep transition occurs too rapidly, resulting in difficulty staying awake, with implications for performance and safety. Although insomnia is almost exclusively defined by patient self-reporting, there is increasing recognition of the importance of objective sleep testing. Hypersomnia, in contrast, is typically defined by measuring the latency to fall asleep during a multiple sleep latency test.

Given the above, there is a need for systems and methods for use in accurately characterizing sleep and transitions thereto. For instance, the ability to track dynamical properties associated with the sleep onset process could provide critical insight into the pathophysiology, aiding in both diagnosis and in treatment.

SUMMARY

The present invention overcomes the drawbacks of aforementioned technologies by providing a system and method for tracking sleep in a subject. In particular, a novel framework is described that allows for integration of both behavioral and physiological information in order to more accurately characterize the dynamic factors that govern the onset and process of sleep.

In some aspects, a statistical model is introduced that can combine various measurements of brain activity, muscular activity, respiratory activity, and other measurements or inputs, to estimate a wake probability for an individual subject. As will become apparent, rather than focusing on a single transition to being asleep, the approach described herein characterizes a degree to which the subject is awake at any point in time. In addition, this framework allows a comparison of sleep dynamics across different populations.

In accordance with one aspect of the disclosure, a method for tracking sleep onset in a subject is provided. The method includes acquiring physiological data using sensors positioned about the subject, and acquiring behavioral data using input provided by the subject. The method also includes generating a statistical model of wakefulness by combining information obtained from the acquired physiological data and behavior data, and estimating a probability indicative of a degree to which the subject is awake at each point in time during sleep onset using the statistical model. The method further includes generating a report indicative of sleep onset in the subject.

In accordance with another aspect of the disclosure, a system for tracking sleep onset in a subject is provided. The system includes a plurality of sensors configured to acquire physiological data and behavioral data from a subject. The system also includes a processor programmed to at least receive the acquired physiological data and behavioral data, and generate a statistical model of wakefulness by combining information obtained from the received physiological data and behavior data. The processor is also programmed to estimate a probability indicative of a degree to which the subject is awake at each point in time during sleep onset using the statistical model, and generate a report indicative of sleep onset in the subject. The system further includes an output for displaying the report.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 1C shows non-limiting sleep monitor example embodiments, in accordance with aspects of the present disclosure.

FIG. 1D shows additional non-limiting sleep monitor example embodiments, in accordance with aspects of the present disclosure.

FIG. 3A shows an example device for acquiring behavioral data, in accordance with aspects of the present disclosure.

FIG. 3B is a graph illustrating example responsive and non-responsive periods during a behavioral task.

FIG. 3C is a graph showing example behavioral and respiratory time traces during the onset of sleep.

FIG. 3D is a graph showing a time trace of squeeze amplitudes associated with the behavioral and physiological time traces of FIG. 3C.

FIG. 3E is a graph showing median squeeze amplitudes computed using the time trace of FIG. 3D.

FIG. 8A is another example spectrogram illustrating alpha power dropout during the sleep onset process.

FIG. 8B is the behavioral response time trace associated with the spectrogram of FIG. 8A.

FIG. 8C is the wake probability curve associated with the physiological and behavior data shown in FIGS. 8A and 8B.

FIG. 8D is the hypnogram associated with data shown in FIGS. 8A-8C.

DETAILED DESCRIPTION

The present disclosure describes a system and method that rely on a statistically principled model framework for characterizing sleep dynamics. Specifically, by combining information obtained from various physiological and behavioral measurements, which can exhibit different signatures across various time scales, a more robust and principled estimate of wakefulness during the process of sleep initiation may be obtained. In some aspects, data associated brain activity, muscular activity, respiratory activity and other physiological processes, along with behavioral responses to a given behavioral task, may be acquired during sleep initiation and utilized to identify a subject wake probability.

As will be appreciated from descriptions below, the provided system and method may find a variety of commercial applications including systems and devices for tracking daily changes in sleep onset for healthy subjects, or diagnosis tools for characterizing pathologies that impact sleep onset, such as insomnia or narcolepsy. Aspects of the present disclosure may also be applicable to tracking the effects of pharmacological agents on sleep, or sleep onset, or tracking drowsiness or wakefulness in people for whom performance readiness is important, such as pilots, military personnel, truck drivers, machine operators, factory workers, and so forth.

Figure 1A:
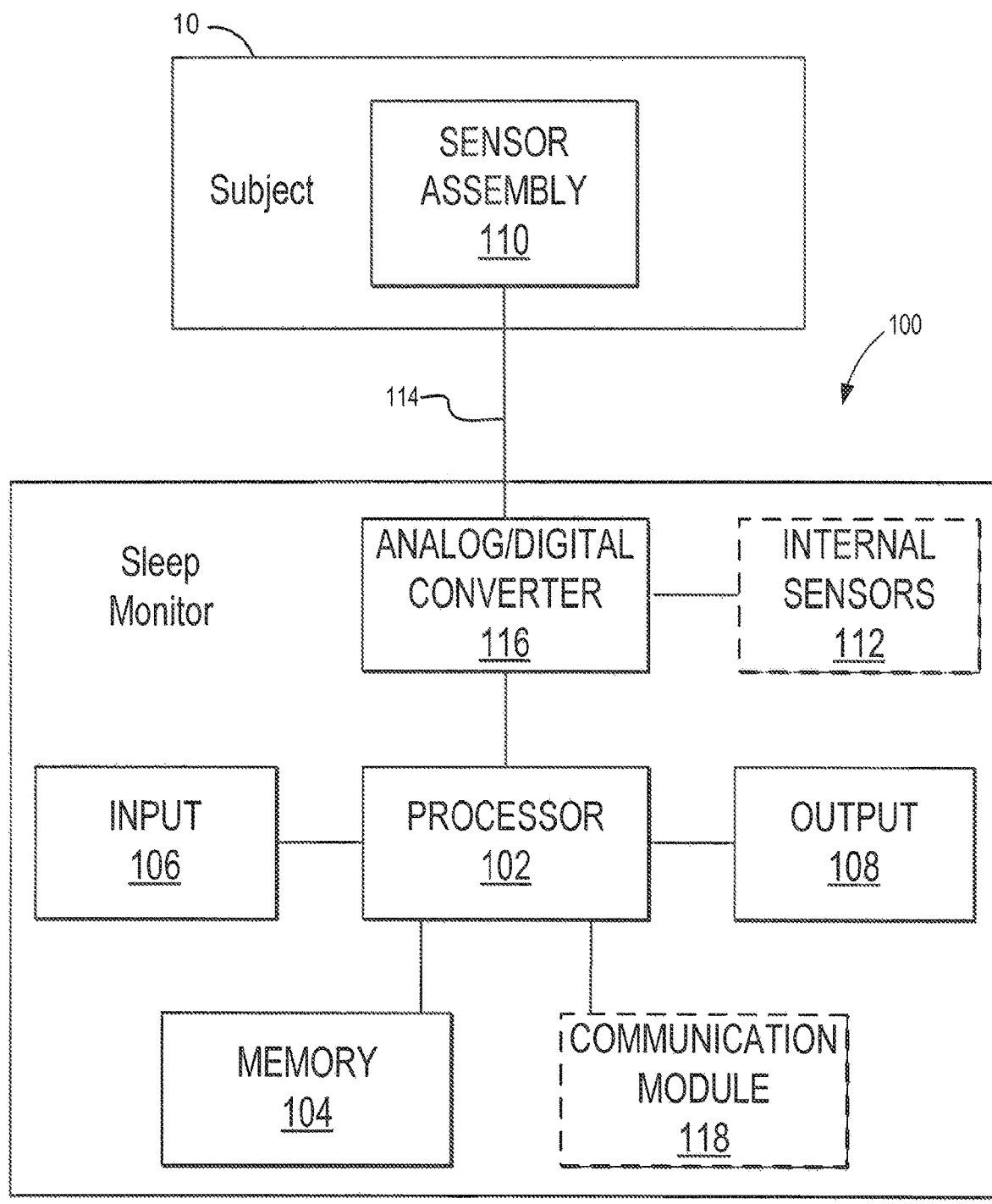
FIG. 1A is a schematic diagram showing an example sleep monitor, in accordance with aspects of the present disclosure.

Turning to FIG. 1, a schematic diagram of an example sleep monitor 100 for use in identifying and tracking wakefulness states, or an onset of sleep for a subject 10, in accordance with aspects of the present disclosure. In general, the sleep monitor 100 may be any device, apparatus or system capable of a wide range of functionality, integrating a variety of software and hardware capabilities. As shown in FIG. 1, in some configurations, the sleep monitor 100 includes a processor 102, a memory 104, an input 106, an output 108, an external sensor assembly 110, and optionally internal sensors 112.

The sleep monitor 100 may operate either independently or as part of, or in collaboration with any computer, system, device, machine, mainframe, database, server or network, as shown in the examples of FIG. 1C. In some aspects, the sleep monitor 100 may be a portable or wearable device or apparatus, for example in the form of a mobile device, tablet, smartphone, smartwatch, and the like, as shown in the examples of FIG. 1D. Alternatively, the sleep monitor 100 may be configured to communicate with such portable device or apparatus, for example, via a communication module 112, implementing a Bluetooth or other wireless communication protocol.

Figure 1B:
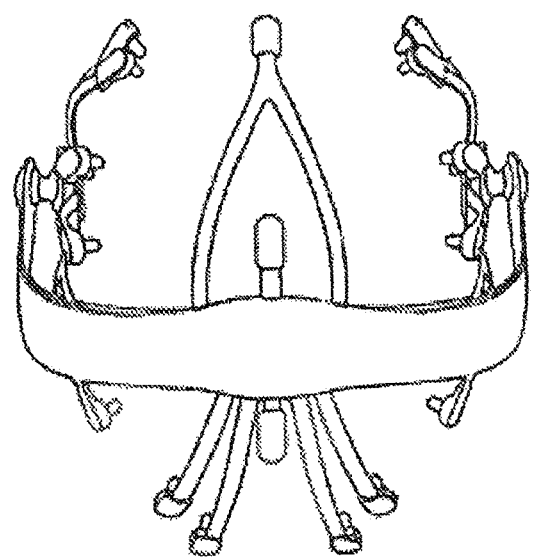
FIG. 1B is an example sensor assembly for acquiring physiological and/or behavioral data, in accordance with aspects of the present disclosure.

The sensor assembly 110 may include any number of active and/or passive sensing elements, and may be configured to measure a variety of signals associated with the subject 10, including brain activity, muscle activity, respiration activity, cardiac activity, eye movement, galvanic skin response, blood oxygenation, as well as motion, pressure, temperature, force, sound, flow, and so forth. Non-limiting examples include electroencephalogram ("EEG") sensors, electromyography ("EMG") sensors, and other sensors. In some configurations, the sensor assembly 110 may be in the form of a device to be worn by the subject 10, as shown in FIG. 1B.

In some aspects, sensors in the sensor assembly 110 may be coupled with any external object or device, such a squeeze ball, or wearable object, such as glove, configured to capture an input or response of the subject 10 to a behavior task. Additionally, or alternatively, such subject 10 response may also be provided via input 106, which can include any sensor(s). For instance, input 106 may include a button, a dial, a mouse, a touch screen, a microphone and the like.

For clarity, a single block is used to illustrate the sensor assembly 110 shown in FIG. 1. However, it should be understood that the sensor assembly 110 shown can include more than one sensing element or sensing element types, such as electrical sensors, oxygenation sensors, galvanic skin response sensors, respiration sensors, muscle activity sensors, pressure sensors, force sensors, temperature sensors, air flow sensors, and so forth, and any combinations thereof. In addition, sensors may be placed at multiple locations about the subject 10, including, but not limited to, the scalp, face, nose, chin, skin, chest, limbs, fingers, and so on.

As shown in FIG. 1, in some configurations the sleep monitor 100 can include internal sensors 112. For example, these can include accelerometers, microphones, cameras, and so on. Such sensors can capture physiological and/or behavior signals similar to or complementary to those obtained from the sensor assembly 110. In some aspects, internal sensors 112 may be configured to obtain surrogate data indicative of physiology or behavior. For instance, accelerometers or microphones may capture the response to a selected task by acquiring vibrational or audio signals generated from subject 10 activity, such as tapping or squeezing. Similarly, accelerometers or microphones may obtain data associated with respiration, or cardiac activity of the subject 10.

Signals generated by the sensor assembly 110 may then transmitted to the sleep monitor 100 over a cable or other communication link 114 or medium, such as wireless communication link, digitized using the analog/digital converter 116, processed using one or more processor 102, and/or stored in memory 104. In some embodiments of the sleep monitor 100 shown in FIG. 1A, all of the hardware used to receive and process signals from the sensors are housed within the same housing. In other embodiments, some of the hardware used to receive and process signals is housed within a separate housing. In addition, the sleep monitor 100 of certain embodiments includes hardware, software, or both hardware and software, whether in one housing or multiple housings, used to receive and process the signals transmitted by the sensors.

The processor 102 may be configured to carry out any number of steps for operating the sleep monitor 100. In addition, the processor 102 may be programmed to pre-process data obtained from the subject 10 using instructions stored in the memory 104. For instance, the processor 102 may be configured to perform signal conditioning or pre-processing, such as scaling, amplifying, or selecting desirable signals, or filtering interfering or undesirable signals. In addition, the processor 102 may be configured to assemble, analyze and identify signatures associated with physiological and behavior signal data in order to characterize sleep dynamics and the onset of sleep. For instance, the processor 102 may be configured to assemble a time-frequency representation using acquired physiological signals, in the form of spectrograms.

In accordance with aspects of the present disclosure, the processor 102 may also be configured to generate a statistical model of wakefulness. In the particular, the processor 102 may combine physiological information, such as brain activity or muscular activity information, and behavioral information, such as responses to a selected task provided via input 106, to estimate a probability indicative of a degree to which the subject is awake at a point in time, as well as confidence intervals for the estimated probabilities. In addition, the processor 102 may also be configured to make comparisons using data or model parameters generated from a population, and stored, for example, in memory 104 or a database. For example, to characterize the sleep or wake states and the sleep onset process, the processor 102 may be configured to compute an average or a median spectral power as a function of frequency and wake probability using data from a population.

In some aspects, the processor 102 may be configured to determine a statistical model using selected or identified sources of data, as well as compensate for missing data. For instance, the processor 102 may determine the availability of data sources such as behavioral data from the subject 10 via input 106, or data obtained using the sensor assembly 110 or the internal sensors 112, or combinations thereof. The processor 102 may then select a specific statistical model of wake probability based on the data sources available at each time point. If a new data source become available or if a data source becomes disconnected or corrupted, the processor 102 may modify the statistical model to account for the new or missing data source.

In yet other aspects, the processor 102 is further programmed to determine a change in sleep onset using estimated probabilities, as well as a sleep phenotype of the subject 10, which is a characterization of the properties of the subject's sleep dynamics. The processor 102 may also be programmed to determine a sleep condition of the subject by comparing probabilities estimated over a sleep period to those of a population, for instance. In addition, the processor 102 may also evaluate an effect of at least one drug on the onset of sleep using estimated probabilities.

In yet other aspects, the processor 102 may be configured to receive a response to a selected task provided by the subject 10 via input 106, or data obtained using the sensor assembly 110 or the internal sensors 112, or combinations thereof, and determine a timing, duration, accuracy and strength of the response. For instance, given a behavior task, where the subject 10 might be instructed to respond in a manner that is timed to respiration, the processor 102 may be configured to determine the accuracy of the response by comparing the provided input with respiration data acquired using the sensor assembly 110 and/or internal sensors 112. In another example, the processor 102 may be configured to determine an amplitude of a response signal obtained, for example, from one or more EMG sensors.

The processor 102 may be further configured to generate and provide a report either intermittently, or in real time, via output 108, which may include a display and/or speaker. The report may be any form, and include any information, including information related to acquired and processed physiological and behavioral data, for instance as time-series waveforms or traces, time-frequency representations, power spectra, response curves, spectrograms, and so on. In some aspects, the report may include an indication or index related to the degree to which the subject 10 is awake at one or more points in time. Also, the report may include descriptions regarding a state of wakefulness or sleep of the subject 10. In other aspects, the report may characterize a sleep onset process. For instance, the report may include estimated wake probabilities, as well as confidence intervals thereof. The report may also include information regarding an identified sleep condition, or phenotype of the subject 10. The report may also include information derived from a comparison between subject 10 data and data obtained from a population.

Figure 2A:
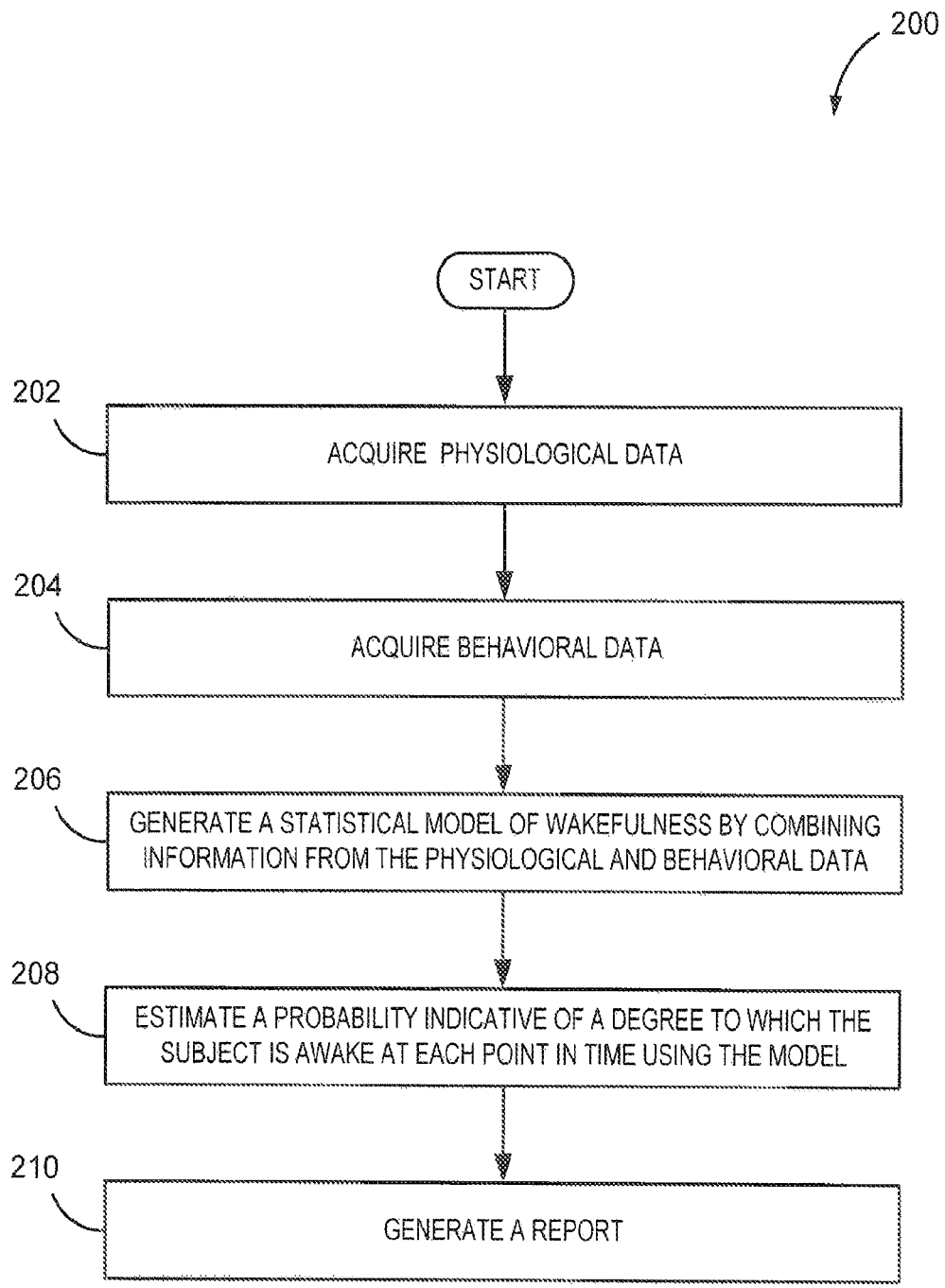
FIG. 2A is a flowchart setting forth steps of a process, in accordance with aspects of the present disclosure.

Turning to FIG. 2A, steps of a process 200 in accordance with aspects of the present disclosure are shown, which may be carried out using any suitable system, such as the sleep monitor 100 described with respect to FIG. 1. At process block 202 physiological data is acquired from the subject. As described, this step can include obtaining, using sensors positioned about the subject, any combination of direct measurements associated with physiological activity, including brain activity, muscle activity, respiration activity, cardiac activity, eye movement, galvanic skin response, blood oxygenation, and so forth. In some aspects, surrogate data may also be acquired and processed at process block 202 to infer such physiological activity.

At process block 204, behavioral data from the subject may be acquired. To acquire the behavior data, a subject may be instructed to perform a specific task at process block 204, such as supplying a response in accordance to externally provided stimuli or cues, such as acoustic, optical, vibrational stimuli or other stimuli. In addition, a timing, duration, accuracy and strength of the response may also be determined at process block 204. Responses can include moving or tapping a finger, pressing a button or screen, grasping or squeezing an object, and so on. Preferably, stimuli and responses that limit or minimize sleep arousal may allow for more accurate characterization of sleep onset dynamics. For example, the subject may be instructed to react to the subject's own breathing, providing a response for each breath.

In some aspects, physiological and behavior data acquisition at process blocks 202-204 may be performed concurrently. This can facilitate a temporal correlation between the data. For example, if a provided response is appropriately timed to a breath, it may be counted as a positive response.

At process block 206 a statistical model of wakefulness may be generated, as will be described, by combining information obtained using the physiological and behavioral data acquired at process blocks 202-204. In some aspects, physiological and behavior data may be retrieved from a memory or database. Then at process block 208, a probability indicative of a degree to which the subject is awake at a given point in time may be estimated using the model.

A report is then generated at process block 210. As described, the report may be any form, and can include information related to acquired and processed physiological and behavioral data, for instance in the form of time-series waveforms or traces, time-frequency representations, power spectra, response curves, and so on. In some aspects, the report may include wake probabilities, or may identify an onset of sleep. The report may track a drowsiness or wakefulness of a subject, or an effect of a pharmacological agent, or a change in sleep onset. The report may also characterize a sleep condition of the subject, such as insomnia or necropsy. The report may also include information obtained from a database or information related to past subject conditions, or conditions of clinical groups or regional populations.

To characterize dynamics of sleep, a statistical state-space model, which relies on a set of state variables that are based on experimental observations, is described herein. In this approach, information obtained from multiple data types may be used to characterize the sleep onset process. To generate the statistical model, random variables representing activity in the systems underlying data observations may be defined. In the following description, behavioral activity, brain activity, namely occipital alpha oscillation power, and delta/theta oscillation power, along with muscular activity, namely EMG, are utilized. It may be appreciated, however, that the present framework may be modified or expanded to include any observables affecting sleep and the onset of sleep.

Specifically, state processes that represent the underlying activity level of the related neural system given the corresponding EEG/EMG observations are modeled. The combined activity levels from the three systems, along with the behavioral task responses, may be used to compute the probability that the subject is awake at each point in time. All model parameters and states may then be fit simultaneously from the experimental data using a particle filter technique. The resulting wake probability curve provides a continuous metric of wakefulness that tracks and characterizes SOP dynamics.

First, state equations, which model the temporal evolution of the state processes $x_t \in \{x_t^m, x_t^\alpha, x_t^{\Delta\theta}\}$ over time, may be defined. In some aspects, state evolution can be modeled as a random walk, reflecting the notion that states cannot change instantaneously, and are related to their past values. The random walk process at time t can be defined as $$\chi_t = \gamma \chi_{t-1} + \varepsilon_x \quad (1)$$

where $\varepsilon_{t_x} \sim N(0, \sigma_{x_t}^2)$ with $\sigma_{x_t}^2 \in \{\sigma_{x_t^m}^2, \sigma_{x_t^\alpha}^2, \sigma_{x_t^{\Delta\theta}}^2\}$ for each corresponding process, and γ is a constant. The state equations constrain the amount that the states can change at each time, which is a function of γ as well as the state variance $\sigma_{x_k}^2$. Herein, data analysis is performed in discrete time, where Δt is the time interval between each of the T observations t={1, . . . , T}.

The values of the state process represent the activity level of the systems underlying the corresponding observations. High values of the state processes represent high activity, while low values represent low activity. The state variances are time varying, and can also be modeled as a random walk $$\sigma_{x_t}^2 = \gamma \sigma_{x_{t-1}}^2 + \varepsilon_{\sigma_x}^2 \quad (2)$$

where $\varepsilon_{\sigma_x^2} \sim N(0, v)$, v and γ are constants. The state variance $\sigma_{x_t}^2$ is also positive.

Figure 4A:
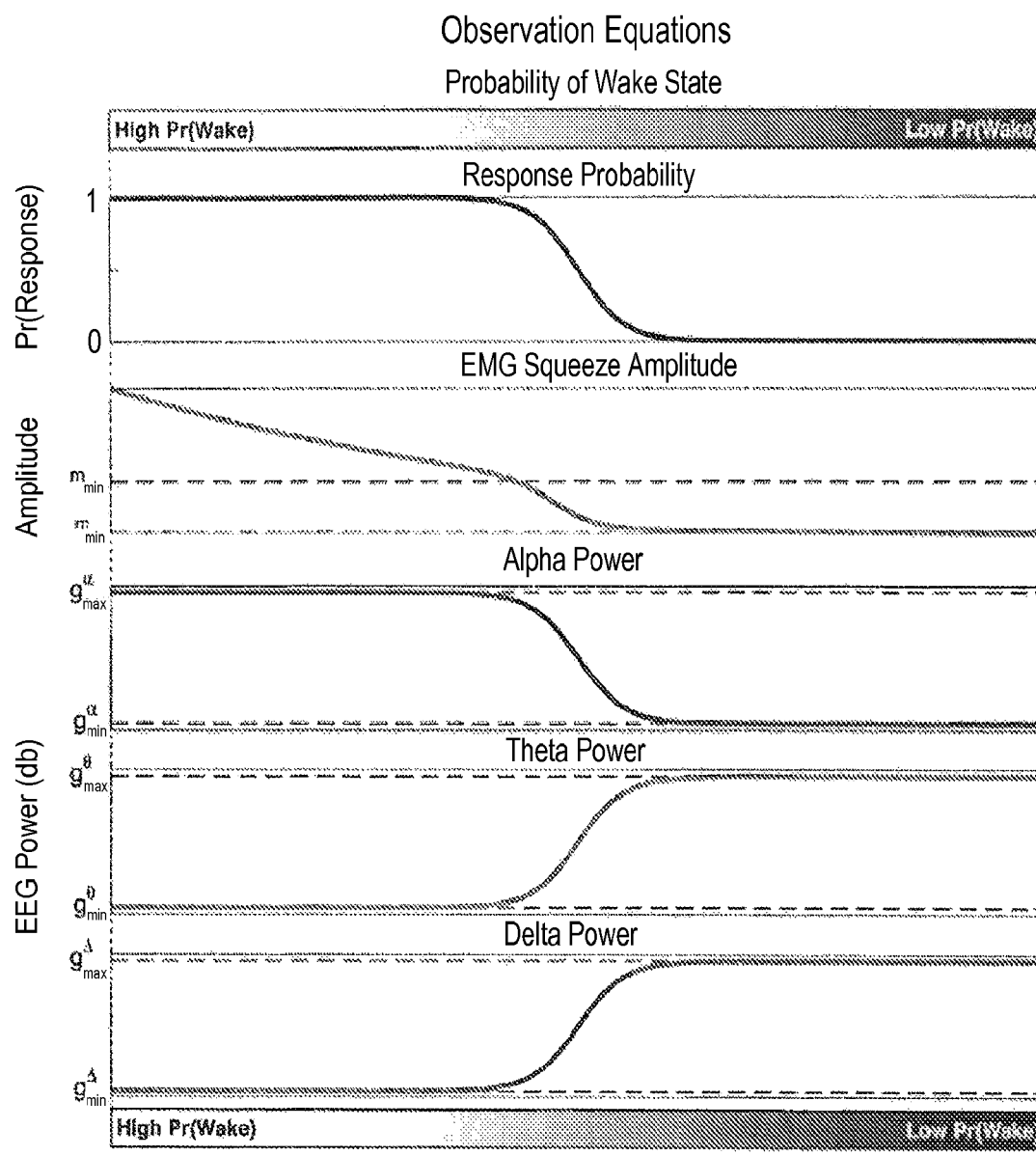
FIG. 4A shows graphs of observation models for response probability, squeeze amplitude, alpha power, theta power and delta power as a function of wake probability.

Given the defined state model and its time evolution, observation models, which specify the relationship between state variables and the observed data, can then be described. A schematic summary of the example forms for the observation models and parameters is shown in FIG. 4A.

As mentioned, one type of behavioral data for use in characterizing sleep can be obtained by monitoring muscle activity, or EMG activity, of a subject while performing a task, such as squeezing an object. For instance, during a task assigned to be timed to respiration, EMG data may be recorded, for example, from the flexor digitorum profundus, which is responsible for finger flexion. If the subject responds correctly, namely by providing input consistent with the respiration cycle, an EMG amplitude for each squeeze may be measured. On the other hand, if the subject responds incorrectly, EMG data associated with an underlying tone of the flexor digotorum profundus muscle, for example, may be acquired. As will be shown, experiments indicated that as subjects fell asleep, the EMG squeeze amplitudes tended to follow an exponential decay pattern. Also, when subjects failed to respond, the EMG amplitude was much lower. Therefore, the relationship between the EMG and motor activity process $x_t^m$ may be modeled such that $A^t$, or the peak squeeze amplitude at time t, has a decaying exponential relationship to $x_t^m$, which drops off rapidly to the underlying level of muscle tones when squeezes cease.

The log of the experimentally recorded EMG squeeze amplitude at time t can be defined as follows:

$$\begin{cases} m_t = \log(A_t) \text{ if there is a breath in } [t, t+1) \\ m_t \text{ is missing data otherwise} \end{cases} \quad (3)$$

A first order linear relationship between the state and the log of the squeeze amplitude may be established, such that $$m_t = \mu_{0,t} + \mu_1 x_t^m + \varepsilon_m \quad (4)$$

where $\varepsilon_m \sim N(0, \sigma_m^2)$, $\mu_1$ is a model coefficient, and $$\mu_{0,t} = m_{rest} + (m_{smin} - m_{rest})\exp(m_{scale} x_t^m) \\ [1+\exp(m_{scale} x_t^m)]^{-1}. \quad (5)$$

The form of the sigmoid is defined by the $m_{rest}$, the resting EMG muscle tone level, and $m_{smin}$ the minimum squeeze amplitude before the drop-off. The variable $m_{scale}$ determines scaling between the squeeze amplitudes and the hidden state.

Similarly, simultaneously recorded EEG activity may be described as a function of the hidden state processes. During the sleep onset process, respective EEG bands have a lower power when underlying systems are inactive, and transition rapidly and plateau at a high level when respective systems are active. Given a set of F unique frequency bands, a general EEG observation model can be defined as sigmoidal function of the state, such that $$g_t^f = g_{min}^f + (g_{max}^f - g_{min}^f)\exp(g_{scale}^f x_t^f) \\ [1+\exp(g_{scale}^f x_t^f)]^{-1} + \varepsilon_g^f \quad (5)$$

where $g_t^f$ is the experimentally recorded EEG power within the $f^{th}$ frequency band at t, $\varepsilon_g \sim N(0, \sigma_g^2)$. The variable $x_t^f$ is the state associated with that given band. The form of the sigmoid may be defined by $g_{min}^f$ and $g_{max}^f$, the minimum and maximum power within that band, and $g_{scale}^f$, which determines scaling between the power and the hidden state.

In this model, two EEG processes may be considered, namely $x_t^\alpha$ and $x_t^{\Delta\theta}$, related to alpha and the joint delta and theta band activities, respectively. Given the general formulation in Eqn. 5, the corresponding observation equations may be defined as follows $$g_t^\alpha = g_{min}^\alpha + (g_{max}^\alpha - g_{min}^\alpha)\exp(g_{scale}^\alpha x_t^\alpha) \\ [1+\exp g_{scale}^\alpha x_t^\alpha]^{-1} + \varepsilon_g^\alpha \quad (6)$$

for the alpha process, and $$g_t^\theta = g_{min}^\theta + (g_{max}^\theta - g_{min}^\theta)\exp(g_{scale}^\theta x_t^{\Delta\theta}) \\ [1+\exp g_{scale}^\theta x_t^{\Delta\theta}]^{-1} + \varepsilon_g^\theta$$

$$g_t^\Delta = g_{min}^\Delta + (g_{max}^\Delta - g_{min}^\Delta)\exp(g_{scale}^\Delta x_t^{\Delta\theta}) \\ [1+\exp g_{scale}^\Delta x_t^{\Delta\theta}]^{-1} + \varepsilon_g^\theta \quad (7)$$

for the joint delta and theta power process. While the delta and theta observation each have their own maximum, minimum, scale and observation noise parameters, they share a common state process, $x_t^{\Delta\theta}$, which combines information from both bands in the state estimation process.

Given knowledge of sleep physiology, during periods of wakefulness, muscle tone and responsiveness to motor tasks are high, while alpha power is high and delta/theta power is low. Therefore, $x_t^w$, the state process related to waking at t, may be defined as a linear combination of the motor, alpha and delta/theta states as follows:

$$x_t^w = \beta_0 x_t^m + \beta_1 x_t^\alpha - \beta_2 x_t^{\Delta\theta} \quad (8)$$

As such, the wake state is correlated with a high motor and alpha process activity, and a low delta/theta process activity. As a subject falls asleep, the motor and alpha process activity will decrease, the delta/theta process activity will increase, and consequently the activity level of the waking state will decrease. In some aspects, $\beta_t = \frac{1}{3}$ so that $x_t^w$ is the mean of the observation state distributions. The variance structure of the observation state distributions will determine the relative contributions of each observation type to $x_t^w$.

Then, $x_t^w$ can be used to compute $p_t^{Wake}$, the probability that the subject is in a waking state at t, as follows:

$$p_t^{Wake} = \exp(x_t^w)[1 + \exp(x_t^w)]^{-1} \quad (9)$$

Figure 4B:
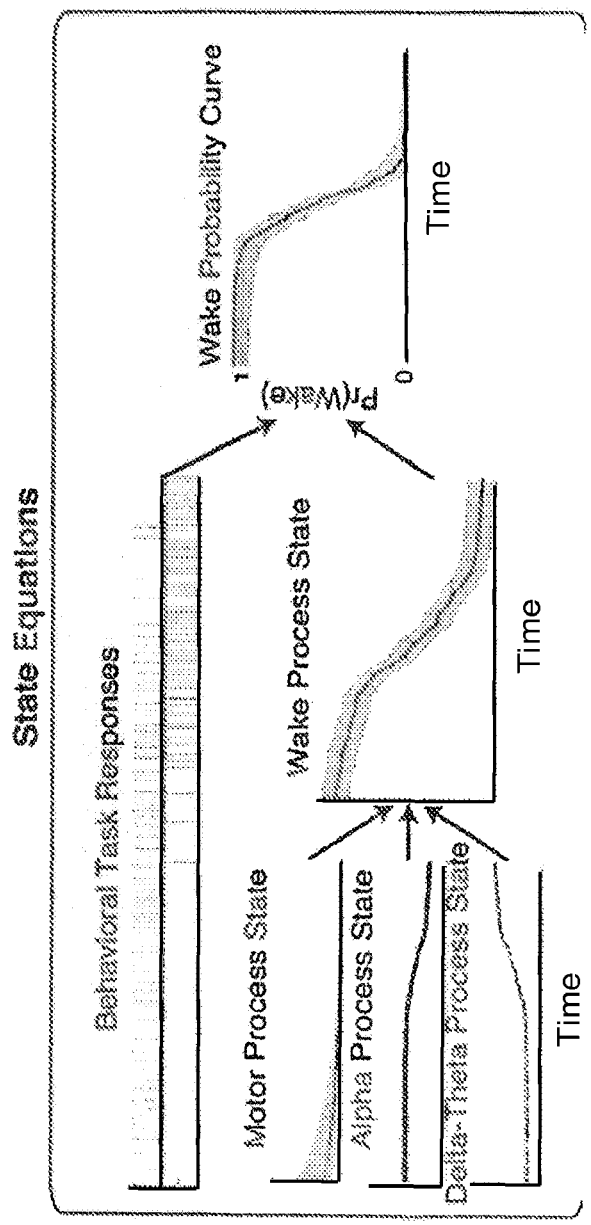
FIG. 4B is a graphical illustration showing how measurement data is combined to generate a wake probability curve.

Herein the distribution of the random variable $p_t^{Wake}$ is referred to as Pr(Wake). A graphical illustration showing the constructions of $p_t^{Wake}$ is shown in FIG. 4B.

Since binary, namely correct versus incorrect, responses to a behavior task are a straightforward correlate of wakefulness, they may be used as observation to fit $p_t^{Wake}$. Specifically, $b_t$, the binary response at time t, may be defined as:

$$\begin{cases} b_t = 1 \text{ if there is a correct response in } [t, t+1] \\ b_t = 0 \text{ if there is an incorrect response in } [t, t+1] \\ b_t \text{ is missing data otherwise} \end{cases} \quad (10)$$

The probability of the behavior response at t, Pr($b_t$) may be modeled as a binomial, as follows:

$$Pr(b_t = k) = (p_t^{Wake})^k (1 - p_t^{Wake})^{1-k}, \quad (11)$$

such that the probability of observing a correct response at t is $p_t^{Wake}$. As a subject falls asleep, $p_t^{Wake}$ will decrease, and the probability of a correct response, such as squeezes on an inhale period of the respiratory cycle, will consequently decrease. In this way, a model is created in which each of the three processes is fit from the bottom up suing EEG and EMG observation. The process estimates may be combined to form $x_t^w$, the waking process, which can be transformed to estimate $p_t^{Wake}$. The value of $p_t^{Wake}$ is simultaneously fit using the behavioral response observation to correspond with the probability of a correct response.

The wake probability, Pr(Wake) may be used at shorthand for $Pr(p_t^{Wake} | b_t, m_t, g_t^\alpha, g_t^{\Delta\theta})$, the posterior density of $p_t^{Wake}$, which represents the probability that a subject is in a wake state, as defined by the model (response probability, EMG amplitude, alpha power high and delta/theta power low) given the observed behavior, EEG, and EMG data. Thus Pr(Wake) serves as a physiologically and statistically principled metric of the degree to which we believe that subject is awake given the observed data. This is useful in tracking sleep onset process dynamics and in aligning data across multiple subjects.

Assuming that correct behavioral responses are a direct correlate of wakefulness, awake subjects will respond to the behavioral task with very high accuracy, and asleep subjects will respond with low accuracy. We explicitly model this in the observation Eqns. 10 and 11, such that Pr(Wake)=Pr($b_t$=1). Therefore, the model output acts an estimate of the probability of response. This is useful for performing a goodness-of-fit analysis, as will be described, in which the degree to which various competing models of wakefulness predict the observed behavioral data are compared.

To estimate the value of model coefficients that are not time-varying, $c \in \{\sigma_{x_t^{\{m,\alpha,\Delta,\theta\}}}^2, \sigma_m^2, \sigma_{g^\alpha}^2, \sigma_{g^{\Delta\theta}}^2, \mu_1, g_{min}^{\{\alpha,\theta,\Delta\}}, g_{max}^{\{\alpha,\theta,\Delta\}}, g_{scale}^{\{\alpha,\theta,\Delta\}}\}$, a random walk may be used namely $$c_t = c_{t-1} + \varepsilon_c \quad (12)$$

where $\varepsilon_c \sim N(0, \nu)$ and $\nu$ is small. This ensures exploration of the parameter space without allowing for large changes in the parameter values. Given state and observation models, as described, a vector of parameter values at time t, namely $\theta_t$, may be defined as follows:

$$\theta_t = \quad (13)$$

$$\left\{ \underbrace{x_t^{\{m,\alpha,\Delta,\theta\}}}_{\text{state value}}, \underbrace{\sigma^2_{\{x_t^m, x_t^\alpha, x_t^{\Delta\theta}, m, g^\alpha, g^{\Delta\theta}\}}}_{\text{state and observe variances}}, \underbrace{\mu_1, m_{\{smin, rest, scale\}}, g_{\{min, max, scale\}}^{\{\alpha,\theta,\Delta\}}}_{\text{linear observation and model coefficients}} \right\}$$

For each $\theta_t$, the posterior density $Pr(\theta_t | b_t, m_t, g_t^\alpha, g_t^\Delta, g_t^\theta)$, which is the probability of the model parameters $\theta_t$ given the data, may be estimated. The posterior density is proportional to $\log(L(\theta_t))$, the joint log-likelihood of all the observations given the parameters.

The log-likelihoods of all the observations may be summed to construct $\log(L(\theta_t))$. Given the binomial log-likelihood for the binary responses $$\log(L(\theta_t)) \propto b_t \log(p_t^{Wake}) + (1 - b_t) \log(1 - p_t^{Wake}) \quad (14)$$

and using Gaussian likelihoods for the continuous-valued observation, the full log-likelihood becomes:

$$\log(L(\theta_t)) = I_{m,t} \{-(m_t - \{\mu_{0,k} + \mu_1 x_t^m\})^2 [2\sigma_m^2]^{-1}\} + \leftarrow \boxed{\text{EMG Amplitude}} \quad (15)$$

$$I_{g^\alpha, t}(g_t^\alpha - \{g_{min}^\alpha + (g_{max}^\alpha - g_{min}^\alpha)\exp(g_{scale}^\alpha x_t^\alpha)[1 + \exp(g_{scale}^\alpha x_t^\alpha)]^{-1}\})^2 [2\sigma_{g^\alpha}^2]^{-1}\} + \leftarrow \boxed{\text{EEG } \alpha \text{ Power}}$$

$$\sum_{f=\{\Delta,\theta\}} I_{g^f,t}$$

$$\{-(g_t^f - \{g_{min}^f + (g_{max}^f - g_{min}^f)\exp(g_{scale}^f x_t^{\Delta\theta})[1 + \exp(g_{scale}^f x_t^{\Delta\theta})]^{-1}\})^2$$

$$[2\sigma_{g^f}^2]^{-1}\} + \leftarrow \boxed{\text{EEG } \Delta, \theta \text{ Power}}$$

$$I_{b,t}\{b_t \log(p_t^{Wake}) + (1 - b_t)\log(1 - p_t^{Wake})\} \leftarrow \boxed{\text{Binary Responses}}$$

where $I_{b,t}$, $I_{m,t}$ and $I_{g^{\{\alpha,\Delta,\theta\}},t}$ are indicator functions for each type of observation at time t. The indicator functions take on the value of 1 if the corresponding observation is present and 0 if it is missing. This provides a flexible likelihood function that is able to handle missing data for any of the observation. Furthermore, any time data is missing, such as due to disconnected EEG or faulty connections, the log-likelihood can be reconstructed from the remaining available data.

To estimate $\theta_t$ at each time, a particle filter technique may be implemented, which is an algorithm based on Bayesian resampling procedure. The idea of a particle filter is to create a large set of parameter vectors, called particles, with different realizations of $\theta_t$ that can evolve over time based on the model equations and observations. The particle filter algorithm may be designed such that the distribution of the parameter vectors is an approximation of the posterior density.

To implement the particle filter, the initial values for each particle may be first drawn from a proposal density $\pi(\theta_1)$, also known as a prior, is a best guess of the distributions of initial conditions for each element of $\theta_t$. Given a set of particles drawn from the proposal density, the time-varying elements in each particle are advanced through the state and parameter one-step prediction equations. If observations are present, the likelihood of each particle given the data is computed using a weight to determine the probability with which the particle will be re-sampled at the next time step. In this way, the distribution of weights acts as $\pi(\theta_{t+1})$, the proposal density for the next time step. The particles are then resampled with replacements according to the new proposal density, and the process is repeated for all subsequent time steps.

An iterative procedure in accordance with aspects of the disclosure is described below. In particular, given a set of P particles, where $\rho_t^i$ is the $i^{th}$ particle at time t, 1) Define $\pi(\theta_0)$ the prior distribution of parameters to be estimated.
2) For each time t={1, . . . , T}, and for all particles $\{\rho_t^1, \ldots, \rho_t^P\}$.
   a) Sample with replacement from the proposal density such that $\rho_t^i \sim \pi(\theta_{t-1})$ for $i \in \{1, \ldots, P\}$.
   b) Update the state and state variance parameters using (1).
   c) Compute a weight vector $w^i$ for each particle such that, $w^i = L(\rho_{t|t-1}^i)$, where $\rho_{t|t-1}^i$ is the particle value after the state updated, and $L(\rho_{t|t-1}^i)$ is the likelihood of the particle given the observations, computed by exponentiating the log-likelihood (5).
   d) Compute $\pi(\theta_t)$, the posterior distribution estimate at time t by normalizing the weights such that $$\sum_{i=1}^{P} w^j = 1.$$

3) The particles $\{\rho_t^1, \ldots, \rho_t^P\}$ act as an estimate of the time-varying posterior distribution $\hat{\theta}_t$.
4) The distribution median and confidence intervals with significance $\alpha$ can be computed using the component-wise $50^{th}$, $\alpha/2$ and $1-\alpha/2$ percentiles of $\{\rho_t^1, \ldots, \rho_t^P\}$, respectively.
5) The wake probability curve is defined as $\hat{\theta}_{1..T}$ the posterior distribution across the entire sleep onset period, and is visualized using the median and 95% confidence bounds of the particles.

A table listing example prior distributions and parameter values is shown below. It may be appreciated that other distributions and values may also be possible.

| Parameter Description | Distribution/Value |
| --- | --- |
| Time resolution | $\Delta t$ = 0.25 sec |
| Number of Particles | P = 10000 |
| State value prior | $x_0^m$, $x_0^\alpha \sim U(0, 3)$, $x_0^{\Delta\theta} \sim U(-3, 0)$ |
| State variance prior | $\sigma_{x,0}^2 \sim U(\rho, 0.5)$ |
| EMG observation parameter | $\mu_1 \sim U(0, 1)$, $m_{s\ min,rest} \sim N(\rho, 0.5)$, where $\rho$ is the 2.5 percentile of the m when $b_k = 1$ and $b_k = 0$, respectively |
| EMG observation noise prior | $\sigma_{\mu,0}^2 \sim U(0, 0.001)$ |
| EEG observation parameter priors | $g_{min,max}^{\{\alpha,\Delta\theta\}} \sim N(\rho, 0.5)$ where $\rho$ is the 2.5 and 97.5 percentile of the power of $g^f$, respectively. $g_{scale}^{\{\alpha,\Delta\theta\}} \sim U(0, 0.5)$ |
| EEG observation noise prior | $\sigma_g^{\{\alpha,\Delta\theta\}2} \sim U(0, 10)$ |
| Random walk parameter | $\gamma = 0.9999$ |
| Coefficient variances | Parameter(s) | Value of v |
| | $\varepsilon_{\sigma^2_{x_k^{\{\alpha,\Delta\theta\}}}}$, $m_{\{min,max,scale\}}$, $g_{\{min,max,scale\}}^{\{\alpha,\Delta\theta\}}$ | 0.01 |
| | $\varepsilon_{\sigma^2_{x_k^m}}$ | 0.02 |
| | $\epsilon_g^{\{\alpha,\Delta\theta\}}$ | 0.1 |
| | $\epsilon_{\sigma_m^2}$ | 0.0002 |
| | $\mu_1$ | 0.004 |

In order to compare the wake probability model to the instantaneous transition models, a Bayesian goodness-of-fit analysis is devised to determine how well each model class estimates the observed behavioral response data across multiple subjects. As each behavior task response is a binary, (correct=1, incorrect=0), the responses may be viewed as Bernoulli trials. Given the behavior data and the estimated probability of response from a specific model m, the binomial log-likelihood of the data, log(L), may be computed as follows:

$$\log(L) = b_t \log(p_{m,t}) + (1-b_t)\log(1-p_{m,t}) \quad (16)$$

where at time t, $b_t$ is the behavioral observation, and $p_{m,t}$ is the estimated response probability from model m, assuming that $Pr(Wake) \propto Pr(Response)$. Computed across all time for all subjects, the total log-likelihood is $$\log(L_{total}(p_m)) = \sum^{subjects} \sum_{t=1}^{T} b_t \log(p_{m,t}) + (1-b_t)\log(1-p_{m,t}) \quad (17)$$

In a Bayesian framework, rather than assigning a constant, the posterior density of response/wake probability of $p_{m,t}$, which is the distribution $f(p_{m,t}|data)$, may be estimated. Consequently, the log-likelihood will also be a distribution.

In order to make a comparison between two models $m_1$ and $m_2$, the difference distribution of the respective log-likelihoods may be estimated as follows:

$$\log(L_{total}(p_{m_1}) - L_{total}(p_{m2})) = \quad (18)$$

$$\sum^{subjects} \sum_{t=1}^{T} b_t \log(p_{m_1,t} - p_{m_2,t}) + (1-b_t)\log(1-(p_{m_1,t} - p_{m_2,t}))$$

The Bayesian credible interval with which the total log-likelihood of $m_1$ is greater than $m_2$ is the proportion of $\log(L_{total}(p_{m_1}) - L_{total}(p_{m2}))$ that rests above 0.

For the wake probability model, $f(p_{m,t}|data) = Pr(Wake)$, which is approximated by the particle filter. The instantaneous transition models, however, classify sleep stage data from the hypnogram into an absolute determination of sleep or wake. To perform a comparison with the wake probability model, the instantaneous transition models may be placed into a Bayesian framework by computing the posterior distribution for each model. An assumption can be made that a waking subject will perform the behavioral task correctly with significance (95 correct response out of 100 trials, for example), and that a sleeping subject will perform incorrectly with significance (5 correct responses out of 100 trials). In the context of a Bernoulli experiment with n trials with k correct Reponses, Bayes' law states that $$\underset{f(p_{m,t}|k)}{\overset{posterior}{\frown}} \propto \underset{f(k|p_{m,t})}{\overset{likelihood}{\frown}} \underset{f(p_{m,t})}{\overset{prior}{\frown}} \quad (19)$$

For the likelihood, a binomial probability model can be used $$f(k|p_{m,t}) \sim \binom{n}{k} p_{m,t}^k (1-p_{m,t})^{n-k} \quad (20)$$

The prior density $f(p_{m,t})$ can be modeled as a beta distribution $$f(p_{m,t}) \sim \text{Beta}(\alpha, \beta) = \frac{\Gamma(\alpha+\beta)}{\Gamma(\alpha)\Gamma(\beta)} p_{m,t}^{\alpha-1} (1-p_{m,t})^{\beta-1} \quad (21)$$

where $\alpha>0$ and $\beta>0$, and $\Gamma$ is the gamma function $$\Gamma(\alpha) = \int_0^\infty x^{\alpha-1} \exp(-x)\, dx.$$

In some aspects, $\alpha=1$ and $\beta=1$ to make the prior uniform and therefore uninformative. The posterior probability density can then be computed as the produce of the likelihood and prior, as follows $$f(p_{m,t}|k) = \frac{\Gamma(n+\alpha+\beta)}{\Gamma(k+\alpha)\Gamma(n-k+\beta)} p_{m,t}^{k+\alpha-1} (1-p_{m,t})^{n-k+\beta-1} \quad (22)$$

Inserting $\alpha,\beta=1$ into Eqn. 22, this simplifies to the beta distribution $$f(p_{m,t}|k) = \text{Beta}(k+1, n-k+1) \quad (23)$$
where
$$\begin{cases} n=100, k=95 \text{ if the binary model indicates Wake} \\ n=100, k=5 \text{ if the binary model indicates Sleep} \end{cases} \quad (24)$$

Given an output of Wake or Sleep from an instantaneous transition model, the posterior distribution of the response probability can be computed using the data.

The log-likelihood distributions may be estimated using a Bayesian Monte-Carlo simulation by repeatedly drawing values of $p_{m,t}$ from a given model's posterior distribution, $f(p_{m,t}|data)$, and inserting the log-likelihood into Eqn. 17. The normalized histogram of the results will approximate the distribution on the log-likelihood. To compute the log-likelihood difference distribution, the same procedure may be followed using Eqn. 18.

In some aspects, steps of a Monte Carlo estimation process of the total log-likelihood distribution are shown below.

1) For each of N samples:
   a) Compute $\log(L_{total}(p_m))$ using Eqn. 17.
   b) If the model is the wake probability mode, $p_{m,t}$ is drawn from the set of particles approximating the posterior distribution.
   c) If the model is an instantaneous transition model, $p_{m,t}$ is drawn from the appropriate Beta distribution given by Eqns. 21 and 23.
2) The log-likelihood distribution is estimated from the histogram of $\log(L_{total}(p_m))$ from the samples
3) The Bayesian credible interval of a can be computed using the $\alpha/2$ and $1-\alpha/2$ sample percentiles In other aspects, steps of a Monte Carlo estimation process of the total log-likelihood distribution difference distribution and Bayesian credible interval are shown below.

1) For each of N samples:
   a) Compute $\log(L_{total}(p_{m_1}-p_{m_2}))$ using Eqn. 18.
   b) If the model is the wake probability mode, $p_{m,t}$ is drawn from the set of particles approximating the posterior distribution.
   c) If the model is an instantaneous transition model, $p_{m,t}$ is drawn from the appropriate Beta distribution given by Eqns. 21 and 23.
2) Compute the histogram of $\log(L_{total}(p_{m_1}-p_{m_2}))$ from the samples
3) The Bayesian credible interval for $\log(L_{total}(p_{m_1}))>\log(L_{total}(p_{m_2}))$ is proportion of $\log(L_{total}(p_{m_1}-p_{m_2}))>0$ The power of the presently described statistical framework lies in the ease with which new data sources may be incorporated into the model, and the ease with which missing data can be handled. For any data source (e.g. behavioral data), so long as there is a model of the relationship between the measurements and wake probability, such observation may be used to determine wake probability, and the log-likelihood will have a single term. If there are multiple simultaneous observations (e.g. behavior and EEG and EMG data), each of which have their own observation models linking the data to their related underling state processes, a joint likelihood may be computed across all processes, thereby producing an estimate of wake probability integrating information from all data sources. If there is missing data, the likelihood terms (using the indicator functions in Eqn. 15) may be ignored to produce a best estimate of the wake probability given the data that is available at that time.

Figure 2B:
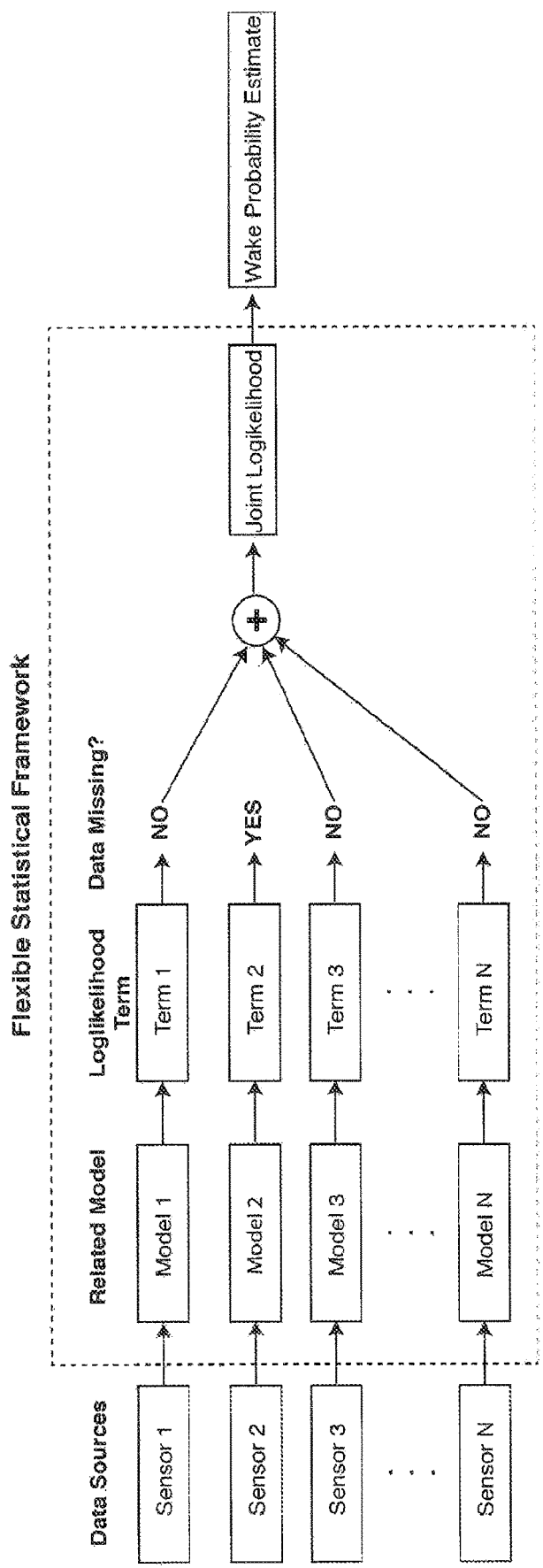
FIG. 2B is a flow diagram illustrating the flexibility of a statistical model to missing data types, generated in accordance with the present disclosure.

This process is illustrated in FIG. 2B, where data obtainable from any number of data sources is modeled using respective models, to produce respective log-likelihood terms. Upon a determination regarding the existence or absence of particular data source, a joint log-likelihood is determined, similar to Eqn. 15, from which a wake probability is then estimated. In particular, after a step of identifying data sources, the physiological processes related to the data sources are identified, which are then used to generate state models for the underlying physiological processes. Then, observation models relating data observations to the underlying physiological state processes are generated, from which a wake process state is then generated based on the combination of the physiological states. Using the wake process state, a wake probability can then be estimated. Thus, in some implementations, a sleep monitoring system, as described, for example with respect to FIGS. 1A-1D, may store the state and models for many different types of data sources. Based on a selected or identified configuration of sensors attached to the sleep monitor, the appropriate likelihood terms and models can then be selected in substantially real-time to provide an estimate of wake probability given all of the available data at any one time.

A flexible likelihood with the ability to handle missing data provides many benefits. One benefit is the ability to include measurements with different temporal resolutions. For example, behavioral responses may be recorded once every few seconds, whereas EEG data can be measured virtually continuously. In this case, the likelihood term for the EEG is used at all times, while the likelihood term for the behavior is used only at the stimulus times. This provides an estimate based on the information from the EEG alone when there is no behavioral measurement, and the combined information from the EEG and behavior when there is a behavioral measurement. Another benefit is the ability to seamlessly handle additional sensors added at any time, namely a new likelihood term being added, or any sensor that is removed or fails at any time, namely the respective likelihood term being removed. Additionally, a benefit is the ability to compute wake probability in situations when limited data is available, for example, if it is only possible to collect EEG. In that case, the likelihood terms related to that data source would be the only terms in the joint likelihood.

The above-described system and method may be further understood by way of examples. These examples are offered for illustrative purposes only, and are not intended to limit the scope of the present invention in any way. Indeed, various modifications of the invention in addition to those shown and described herein will become apparent to those skilled in the art from the foregoing description and the following example, and fall within the scope of the appended claims.

EXAMPLE

Methods

Ten healthy right-handed subjects (5 men and 5 women) with ages ranging 19-32 years (mean: 25.8, std: 5.09) and BMI<30 slept for two consecutive nights. Subjects were screened to ensure a regular sleep schedule and no history of sleep disorder, psychiatric problem, or neurological disease, as well as to ensure no history of tobacco, or prescription/recreational drug use. A one night of home monitoring was performed to exclude obstructive sleep apnea (OSA) screening (using a threshold of AHI<5, and RDI<15) (WatchPAT, Itamar Medical). A trained technician analyzed the experimental PSG data following the first experimental night, and one subject was excluded after failing to meet the OSA criteria on the first night). Urine tests for drug use (Xalex Multi Drug Kit for 10 Drugs) occurred at screening and prior to each experimental night. Female subjects were also screened for pregnancy.

Subjects were fit with a high . . . density (64-channel) EEG cap, as well as standard clinical PSG sensors including PTAF, airflow, abdominal belt, and eye, chin, and limb electrodes. EMG data were bandpass filtered between 10 and 70 Hz with the addition of a notch filter at 60 Hz. Airflow and abdominal belt data were bandpass filtered between 0.1 and 12 Hz. EEG and DC channel data were unfiltered. Multitaper spectrograms of the EEG data from 8 occipital channels were computed with 6 s temporal windows and 0.25 s overlap, a time-bandwidth product of 3, and 5 tapers. Delta, theta, and alpha power were defined as the total multitaper spectral power in 0.5-5 Hz, 5-8 Hz, and 8·12 Hz frequency bands, respectively, of the median of the 8 occipital EEG channel spectrograms. It should be noted that the frequency band definitions for alpha, delta, and theta bands are not universally standardized, and thus vary between subfields within in the electroencephalography literature. Visual staging of sleep data was performed prior to the statistical analysis by an experienced clinical sleep technician using contemporary AASM guidelines.

In order to track the course of sleep initiation, a continuous-valued metric of wakefulness was created that was based on simultaneously observed data from multiple modalities, and for which statistical confidence can be computed. To do so, a task was created that consisted of multiple objective behavioral observations related to wakefulness, which could be tracked across the sleep initiation process. Standard behavioral response tasks used previously involving external audio, visual, or tactile stimuli are potentially arousing and may perturb sleep initiation. Therefore, in the present approach, a self regulated behavioral task centered on breathing was utilized, allowing for repeated trials that can persist throughout the sleep initiation process, and free from arousing external stimuli.

Subjects were given a small, 2 oz, gel-filled stress ball to hold in their dominant hand. They were instructed to breathe normally with eyes closed, and to gently squeeze the ball on each inhale and release on each exhale. Thus, each breath acted as a stimulus, and each corresponding squeeze (or lack thereof) was the corresponding response. A correct response was defined as the squeeze centered on a respiratory inhale, and an incorrect response was either a lack of response or an incorrectly timed squeeze. Subjects were instructed to start the task as soon as the lights were turned out.

An additional bipolar adhesive EMG sensor recorded activity of the flexor digitorum profundus (FDP) responsible for finger flexion. Subjects also were fit with a glove designed with a force sensitive resistor (FSR) embedded in the index finger, to measure finger flexion during the behavioral task [FIG. 3A]. Both the glove and FDP EMG sensors were configured to detect even gentle squeezes (on the order of the force required for a mouse click), thereby allowing subjects to perform the task with minimal effort or muscle fatigue.

The traces from the glove and FDP EMG were time-aligned with simultaneously recorded PSG respiratory metrics (PTAF, airflow, and abdominal belt) [FIGS. 3B and 3C]. These recordings were then visually scored. Specifically, the apex of each respiratory inhale was considered a trial. If a squeeze (visually scored using the EMG/glove activity) was present during an inhale (visually scored using the PTAF, airflow, and abdominal belt), the trial was scored as correct [FIG. 3B, green regions 302]. If there was no visible response or a misaligned squeeze, the trial was scored as incorrect [FIG. 3B, red regions 304]. Periods including motion artifacts, signal degradation due to temporary sensor disconnection, or any other uncertainties in the signal were left unscored and treated as missing data in subsequent analyses. Scoring was started at the first sequence of trials following lights out that began with at least 3 consecutive correct responses. Scoring was stopped 10 minutes following the last correct response. Some subjects reported difficulty performing the task while they adjusted to wearing the full EEG/EMG/PSG montage. After excluding data from four nights with poor task compliance due to difficulty habituating to the extensive sensor montage, the remaining 16 nights from 9 subjects were processed using our algorithm. A wake probability curve was generated for each night.

Along with each behavioral response, EMG activity was simultaneously recorded in the FDP muscle—including the amplitude of each squeeze accompanying a correct response [FIG. 3D]. To measure the magnitude of the squeeze, the amplitude envelope of the EMG was computed using a Hilbert transform. The mean amplitude was then computed in a 1 second window centered around the trial time [FIG. 3E]. In tracking EMG data over the course of the SOP, the EMG squeeze amplitudes decayed until the correct responses stop entirely, similar to continuous observations of muscle activity using a dead man's switch device. Thus, the EMG squeeze amplitudes provide a continuous-valued metric of both muscle tone and of wakefulness.

In addition to behavioral task data, EEG data was also simultaneously recorded from each of the subjects. Specifically, continuous correlates of sleep in the EEG were utilized for analysis, namely power in delta, theta, and alpha frequency bands, which contribute information about different neurophysiological systems in play during the SOP. With physiological and behavioral sources of information, a method was devised for integrating them into a single, statistically principled model of wakefulness during the SOP.

In particular, a wake probability, Pr(Wake) was defined as the posterior probability, or the probability of the model given the observed data, that certain conditions for the wake state are met. For instance, such conditions included whether the subject was responding correctly, the EMG amplitude and alpha power were at their highest, and delta power and theta power were at their lowest. In this case, Pr(Wake) approaches 1. This allowed use of Pr(Wake) as a metric representing the degree to which a subject is believed to awake. Moreover, the formulation of Pr(Wake) was such that it also represented the probability of correctly responding to the behavioral task. Given this formulation, wake probability model was fit to EEG, EMG, and behavioral data to track Pr(Wake) over time. The time-varying estimate of Pr(Wake) was defined as the wake probability curve.

To implement this approach, as described, a Bayesian state-space modeling framework [FIG. 4B] was utilized. State-space modeling allows estimation of non-observable quantities, such as the probability of the subject being awake, from observations that can be directly measured, including EEG, EMG, and behavioral data. Specifically, observations were modeled as a function of state processes that represent the level of activity in their underlying systems. Although the state processes are not directly observable, their values can be inferred from the data given the structure of the model.

In particular, three state processes were generated, namely a motor activity process state $x^m$, an alpha process state $x^\alpha$, and a delta-theta process state $x^{\Delta\theta}$. For each of the state processes, a state equation, describing the way the states evolve over time, was defined. The state equations were designed to reflect observations of subjects during sleep. In the model states were defined such that they would not change instantaneously, and would be related to past values. Specifically, the motor activity process $x^m$ represents the degree of wakefulness estimated from the amplitude of the EMG during the behavioral task. As a subject becomes drowsy, the force of the squeezes decreases and eventually reverts to the underlying muscle tone [FIG. 3D-E]. The alpha process $x^\alpha$ represents the degree of wakefulness estimated from the spectral power in the EEG alpha band. As a subject falls asleep, the alpha power decreases. If the subject awakens, the alpha power would return. In addition, the delta-theta process $x^{\Delta\theta}$ represents the degree of wakefulness estimated from the spectral power in the EEG delta and theta bands. As a subject enters NREM sleep, the delta and theta increase. If the subject awakens, the power in delta and theta would rapidly decrease. The model was formulated such that each state process could change independently, reflecting the asynchronous dynamics found in cortical and subcortical systems generating EEG rhythms throughout the SOP. The wake probability was then defined a function of the linear combination of the three states, with $x^m$ and $x^\alpha$ having a direct relationship to the wake probability, while $x^{\Delta\theta}$ having an inverse relationship to the wake probability.

The observation equations, which describe the relationship between the experimental observations (EMG, alpha, delta, theta, and binary responses) and the underlying state processes was then defined [FIG. 4A]. Each observation equation was constructed so that the value of the state process was high when the data indicated high activity, and low when the data indicated low activity. An observation equation relating behavioral response to wakefulness was also defined, such that response probability was directly proportional to Pr(Wake).

Together, the state and observations defined a framework relating experimental observations to the underlying behavioral and physiological processes, and provided an explicit model for how the aggregate activity of these processes relate to changes in behavior. Using the state and observation equations together with the data, hidden states and model parameters were simultaneously estimate at each time, using a particle filter, which is a Bayesian resampling method. The particle filter evaluates all the data observations in context with model equations and computes the maximum-likelihood state and parameter values. Herein, the particle filter output represented an estimate the full distribution of the posterior probability of the wake probability model, given the observed EEG, EMG, and behavioral data.

The wake probability model allows characterization of the SOP for an individual subject on a given night of sleep. However, it also allows comparison of the SOP for different subjects in a principled manner. This is because the value of Pr(Wake) provides a common point of wakefulness for the alignment of the physiological data across subjects.

To characterize the population dynamics of the EEG during the SOP, the EEG spectrum of the population was computed as a function of Pr(Wake). Specifically, the median spectrum was computed over all subjects and nights at each value of Pr(Wake). Values of Pr(Wake) were considered in discrete bins of width 0.0025 between 0 and 1. The group-level spectrum, or SOP population spectrogram, was plotted as a function of Pr(Wake), appearing similar to a traditional spectrogram, but displaying median population spectral power as a function of frequency and Pr(Wake), rather than frequency and time. Since Pr(Wake) also represents response probability, this analysis stherefore characterized the average EEG spectrum dynamics during the SOP as behavioral response probability declines during the transition from wakefulness to sleep.

The SOP population spectrogram allows for summarizing an SOP phenotype for a given population of subjects. Furthermore, the difference in the SOP phenotype of two populations may also be quantified by comparing their respective population spectrograms. To do so, a bootstrap procedure was utilized to compute the difference distribution for each frequency-Pr(Wake) bin using 10,000 iterations per bin. A frequency-Pr(Wake) bin was considered to be significantly different between populations if zero fell outside the $2.5^{th}$ and $97.5^{th}$ percentiles of the difference distribution.

Since wake probability is a quantity not directly observable during the SOP, standard analyses of measurement error are not possible, as there is no ground truth against which Pr(Wake) can be compared. Therefore a likelihood analysis was performed instead to assess how well a particular model of the SOP described the behavioral task data. Bayesian Monte Carlo procedures were used to compute the likelihood of a given model, as well as compare the likelihoods of two competing models, as described.

Clinically, the SOP is typically characterized by hypnogram-based definitions of a single moment of sleep onset. By definition, any characterization of a "sleep onset point" cleaves SOP dynamics into a unitary wake state prior to the sleep onset point and a unitary sleep following that point. Thus, while never stated outright, any definition of a sleep onset point imposes an instantaneous transition model on the SOP. Since these models assume an instantaneous wake/sleep transition, it follows that they also assume an instantaneous change in behavioral task performance. Therefore a probability curve analogous to the wake probability curve can be constructed for any instantaneous transition model by conservatively assuming that the subject should respond correctly with significance (95% accuracy) when deemed awake, and incorrectly with significance (5% accuracy) when deemed asleep. A comparison between these curves and the wake probability curve can then be made in order to assess the relative goodness-of-fit.

To perform the goodness-of-fit analysis, the likelihood distributions were computed for the wake probability model and four different instantaneous transition models using the behavioral data across all subjects for all nights. The confidence (Bayesian credible) interval with which the wake probability model likelihood differed from that of each instantaneous transition model was computed. Since the wake probability model incorporates information from the behavioral data, the posterior distribution from the time step prior to the behavioral observation was utilized in all of the goodness-of-fit analyses to ensure that use of true behavioral response in the wake probability model formulation did not unfairly affect the results.

Results

Figure 5A:
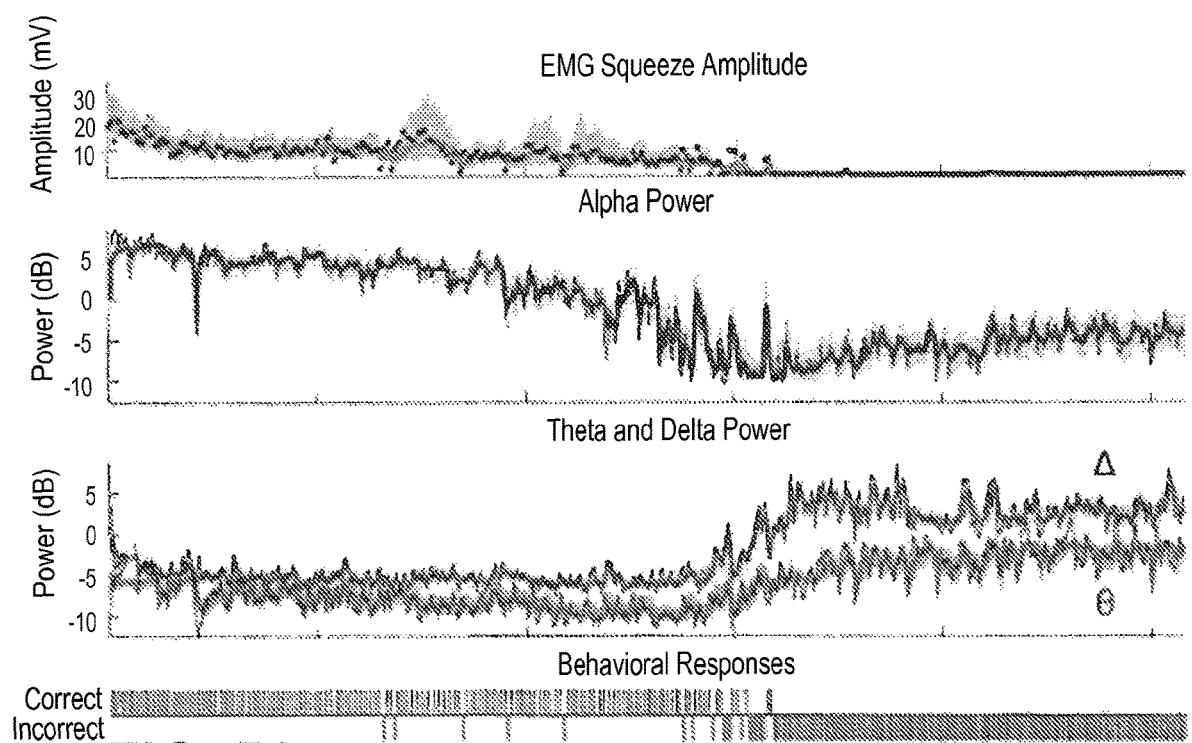
FIG. 5A shows graphs of example of the model fit from physiological and behavioral data acquired from a subject during the onset of sleep.
Figure 5B:
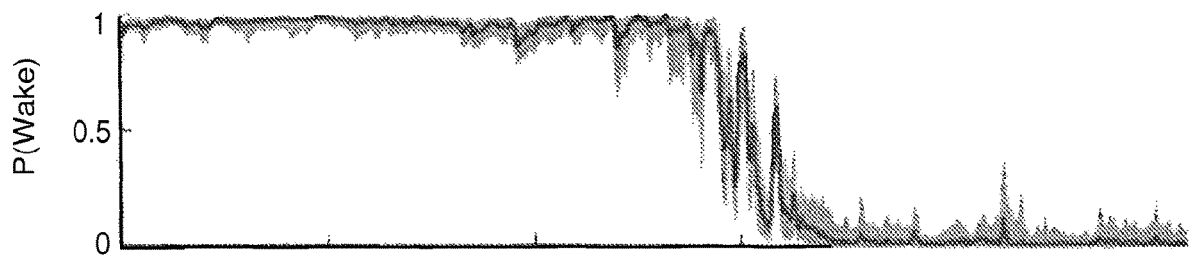
FIG. 5B is a graph of an example probability curve computed in accordance with aspects of the present disclosure using the physiological and behavioral data of FIG. 5A.
Figure 5C:
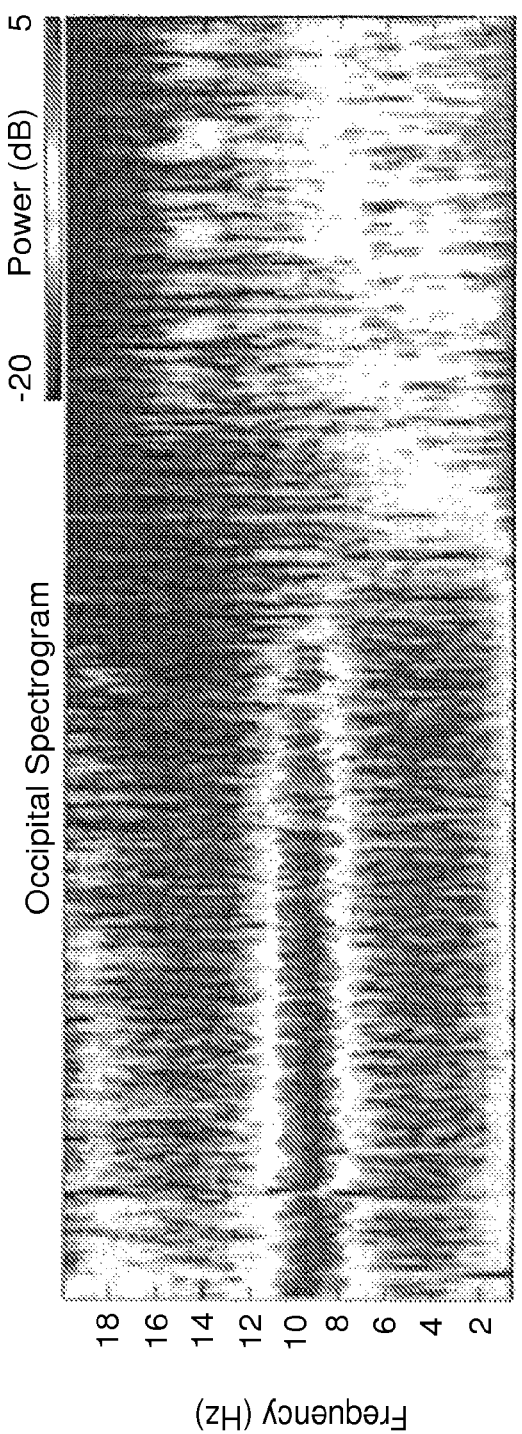
FIG. 5C is an example spectrogram illustrating electroencephalogram ("EEG") features associated with occipital brain activity during the onset of sleep.
Figure 5D:
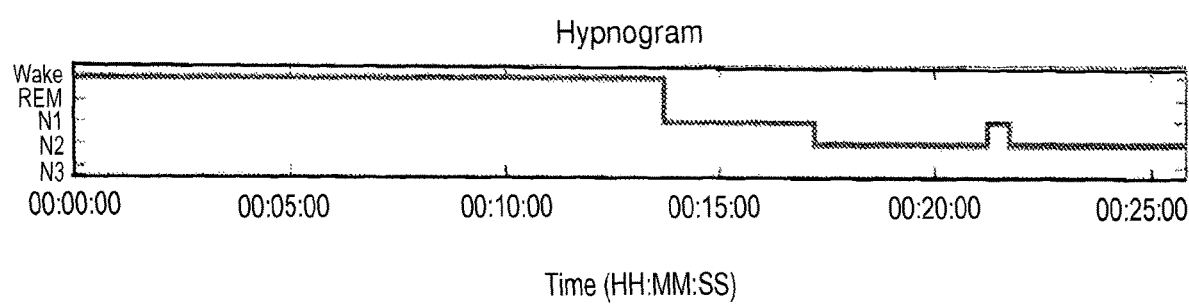
FIG. 5D is a hypnogram associated with data shown in FIGS. 5A-5C.

In the present model of the SOP, a subject's probability of wakefulness is based the combined information from both behavioral and physiological observations. FIGS. 5A-5D shows an example of the model being fit to physiological and behavioral data acquired from a subject. Specifically, FIG. 5A shows the raw EMG squeeze amplitude, the alpha, theta and delta power data, along with model estimates and 95% confidence intervals. The wake probability curve shown in FIG. 5B was estimated using information from both behavioral and physiological data, and therefore integrated features of both modalities. This is most clearly demonstrated by examining the wake probability curve [FIG. 5B] with the corresponding raw data [FIG. 5A], EEG spectrogram [FIG. 5C], and clinical hypnogram [FIG. 5D].

The behavioral data started with a train of correct responses while the subject was awake with eyes closed. This period was followed by an increased number of incorrect responses, which coalesced into a train of incorrect responses. Correspondingly, the EEG data transitioned from a pattern with a strong alpha oscillation and minimal delta or theta during high wakefulness, to a pattern with intermittent alpha and rising energy in delta and theta bands. Eventually, the EEG was dominated by delta and theta power, and the alpha oscillation disappeared. During the SOP, the alpha power was observed to decrease in a sigmoidal fashion, while the delta and theta power increased in a sigmoidal fashion. The EMG amplitude decayed exponentially at first, followed by a sigmoidal trajectory. These trajectories are in line with our model observation equations, depicted in FIG. 4A and detailed above. As appreciated from FIG. 5A, the model estimates tracked the raw data closely.

The structure of the wake probability curve appeared to successfully integrate features of the behavioral and physiological observations. In particular, for roughly the first 13 minutes of the SOP, the wake probability curve was close to a value of 1, with a narrow confidence interval. This agrees with large number of correct behavioral responses, strong alpha mode in the spectrogram, and hypnogram score of wake. Shortly after 13 minutes into the SOP, the probability curve fluctuated several times before settling into a low Pr(Wake) at around 17 minutes. After 17 minutes, the behavioral responses were exclusively incorrect, the EEG alpha power had dropped out, with a sharp rise in delta and theta power, a low value for Pr(Wake). Moreover, the rise in Pr(Wake) between 21 and 22 minutes aligns directly with the hypnogram, which showed a change from Stage 2 to Stage 1 and back during the same interval.

By examining the transition period in this same subject in greater detail, further insight can be gained into how the behavioral and EEG data are combined to estimate the wake probability curve. FIGS. 6A-D show a close up of the data shown in FIGS. 5A-D focused on a period of 6 minutes around sleep onset.

Figure 6A:
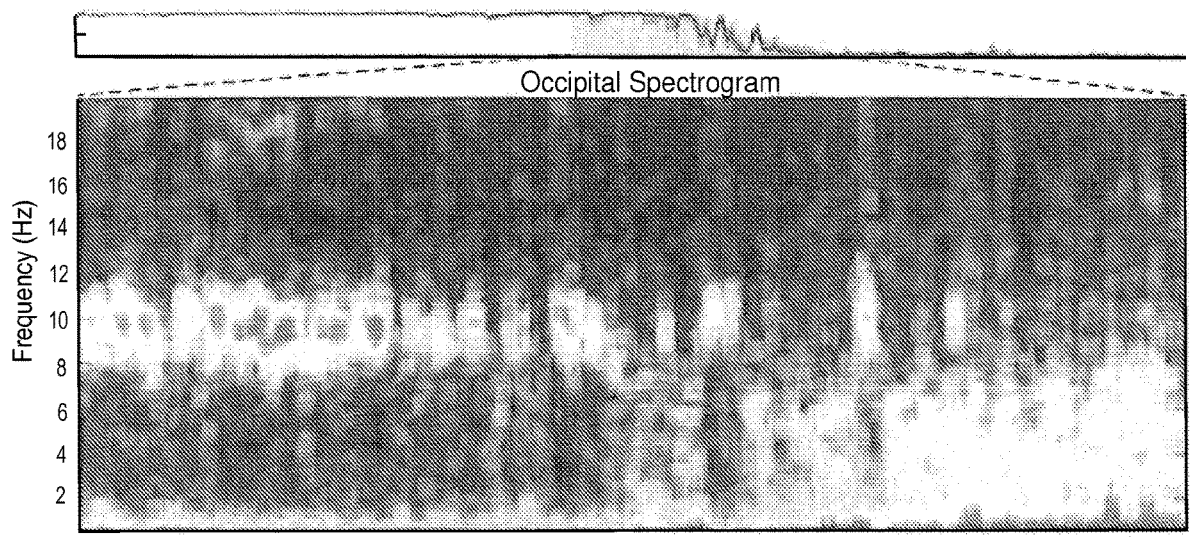
FIG. 6A is the spectrogram of FIG. 5C focusing on a narrow time window around the onset of sleep.
Figure 6B:
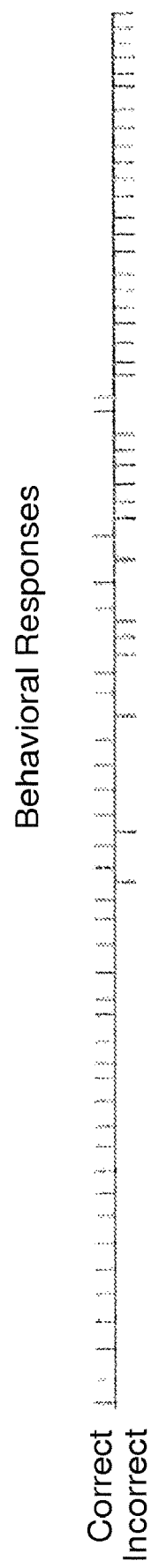
FIG. 6B is the behavioral response time trace shown in FIG. 5A focusing on a narrow time window around the onset of sleep.
Figure 6C:
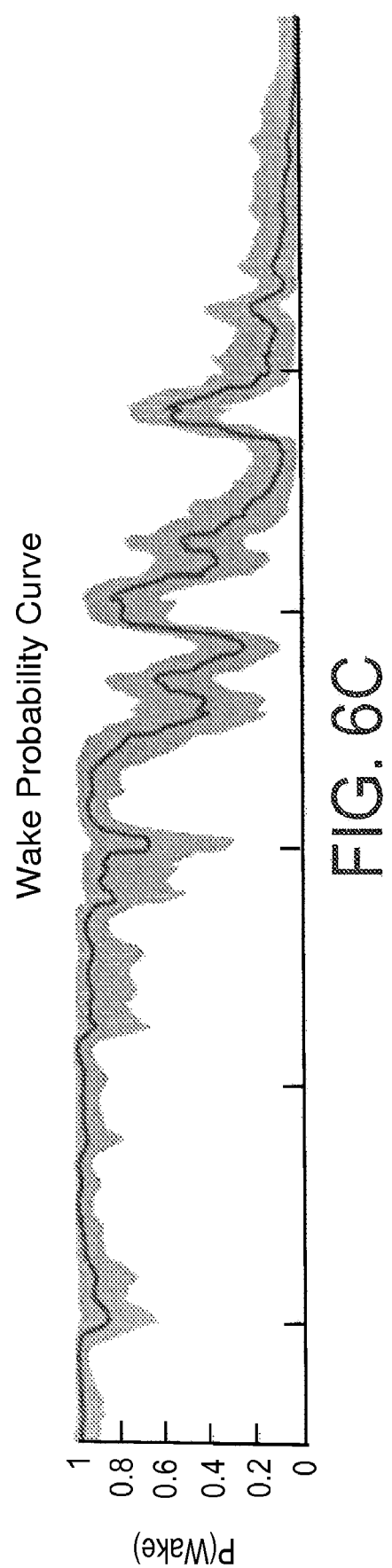
FIG. 6C is the wake probability curve shown in FIG. 5B focusing on a narrow time window around the onset of sleep.
Figure 6D:
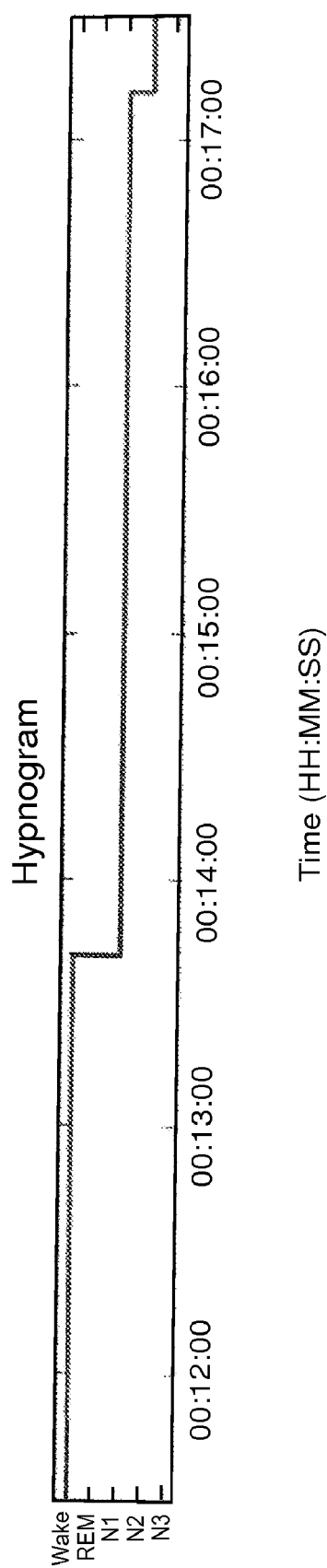
FIG. 6D is the hypnogram shown in FIG. 5D focusing on a narrow time window around the onset of sleep.

The examined period begins with a string of 22 consecutive correct behavioral responses [FIG. 6B]. Since correct responses indicate wakefulness, this is associated with a Pr(Wake) value very close to 1. However, during the same time, the alpha power [FIG. 6A] was observed to disappear sporadically, suggesting that the subject was more ambiguously awake. In the model, low alpha and high delta-theta power imply Pr(Wake) towards 0. As a result, Pr(Wake) values appeared less than 1 during these times. While the behavioral responses were correct, loss of alpha power indicated a reduced wakefulness, resulting in a lowering of Pr(Wake) and an increase in the uncertainty of the estimate (as indicated by wider confidence bounds).

As the subject transitioned through the SOP, the number of incorrect responses increased, the alpha diminished progressively, and delta and theta appeared and began to coalesce into prominent oscillations. This period was marked by an alternation between alpha and delta/theta activity, and continued until the alpha power disappeared, the delta/theta was high, and all the responses were incorrect. Consequently, there were peaks in Pr(Wake) where there was high alpha power, low delta/theta power, and correct responses, and troughs where the opposite was true. The magnitude of these peaks and troughs was based on the degree to which the aggregate data indicated that the subject is awake. The confidence bounds were related to the degree to which all of the data was in agreement. Also, compared to the traditional clinical hypnogram (scored in 30 s epochs) [FIG. 6D], the wake probability curve characterized the transitional period of the SOP with a much higher temporal resolution. As appreciated from the example of FIGS. 6C and 6D, a wake probability curve depicts a continuum of wakefulness, rather than the discretized states associated with a hypnogram.

The transition from wake to sleep can be fragmented—most notably in patients suffering from difficulties with sleep initiation, but also in healthy people. FIGS. 7A-7D illustrate by showing data from a second experimental night from the same subject shown in FIGS. 5 and 6. Rather than the smooth transition seen the first experimental night, the subject experienced brief arousal period 700 in the middle of the SOP. The wake probability curve shown in FIG. 7C captures both the slow transition from wake to sleep, as well as the rapid changes in wakefulness during the arousal period 700.

Figure 7A:
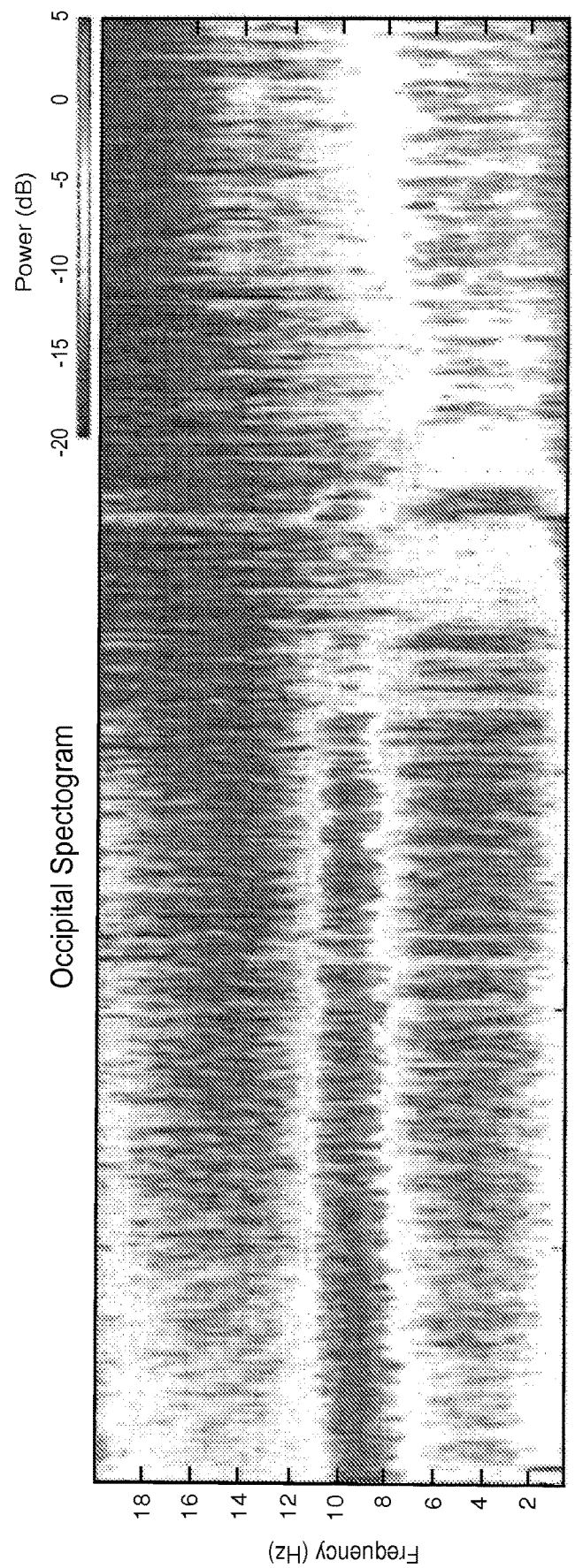
FIG. 7A is another example spectrogram illustrating a fragmented onset of sleep.
Figure 7B:
FIG. 7B is the behavioral response time trace associated with the spectrogram of FIG. 7A, illustrating a return of responsiveness during the sleep onset process.
Figure 7C:
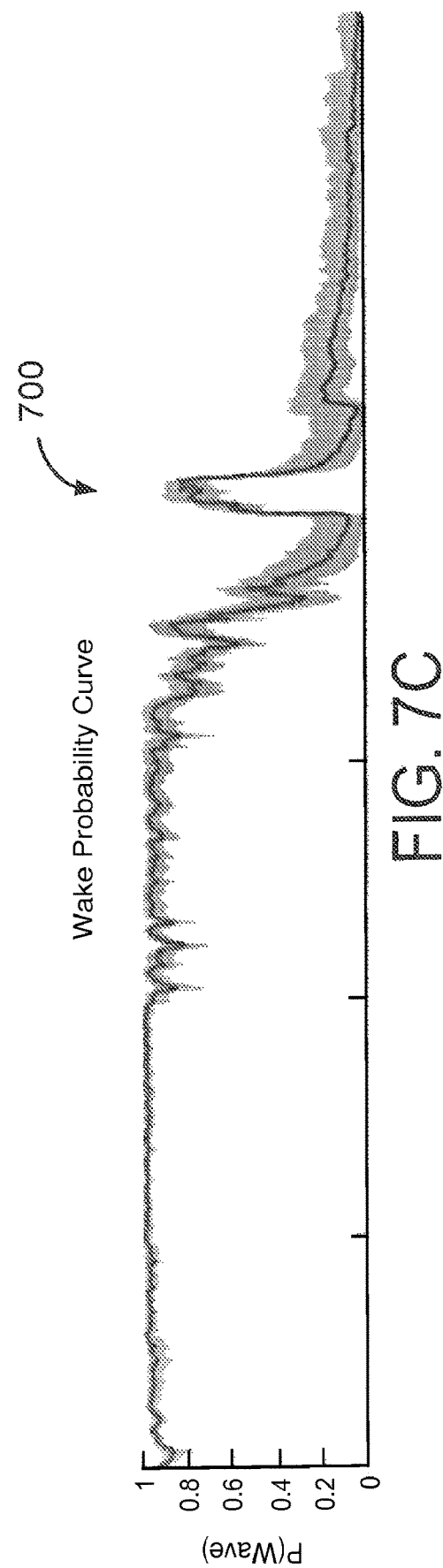
FIG. 7C is the wake probability curve associated with the physiological and behavior data shown in FIGS. 7A and 7B, illustrating an increase in the wake probability during the sleep onset process.
Figure 7D:
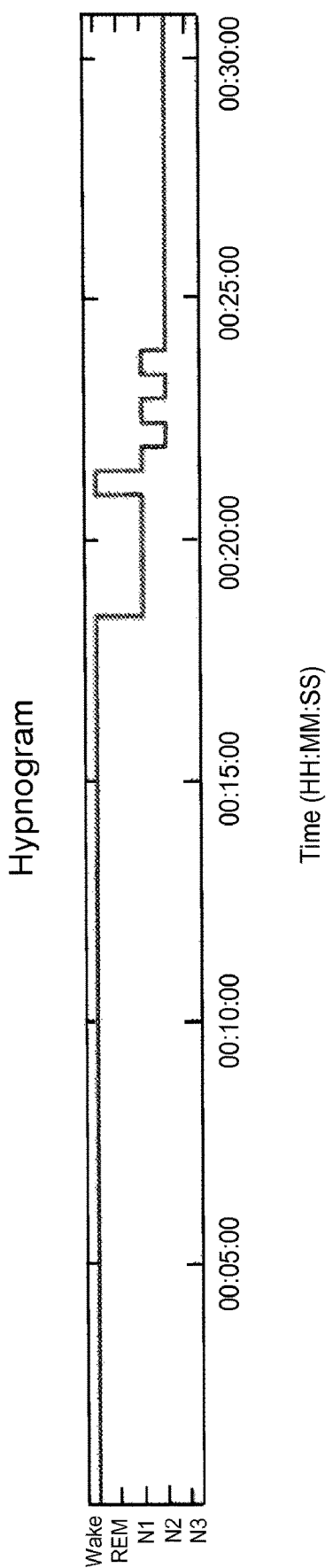
FIG. 7D is the hypnogram associated with data shown in FIGS. 7A-7C.

As in the subject's first night, the SOP began with trains of correct responses [FIG. 7B], a strong alpha mode, and low delta and theta [FIG. 7A], which resulted in a high Pr(Wake) value [FIG. 7C]. The alpha mode then become sporadic, coinciding with an increase in incorrect responses. Next, Pr(Wake) dropped towards 0, as a result of train of consecutive incorrect responses, the alpha mode disappearing, and a dramatic increase in the theta power and rising delta power. Suddenly, at the onset of the arousal period 700, correct responses began again, the alpha mode returned, and the delta and theta dropped off. Given this physiological and behavioral information, Pr(Wake) ascended rapidly towards 1. After approximately 1 minute, the responses become exclusively incorrect again, and the alpha power disappeared. The delta and theta power rapidly returned to their pre-arousal levels, continuing to increase for the rest of the SOP. The wake probability curve tracks the drop in Pr(Wake) and the dynamics for the rest of the SOP. Again, the wake probability curve structure agreed strongly with the structure of the hypnogram [FIG. 7D], but provided greater temporal resolution and finer granularity in the state estimate.

In the preceding illustrative examples, there was strong agreement between the behavioral and physiological data. In practice, however, there is neuro-physiological heterogeneity observed—even within healthy subjects—such that there is often a great disparity between behavioral and physiological metrics of sleep onset. In this section, the manner in which wake probability curve characterizes such situations is illustrated.

FIGS. 8A-F show the results from another healthy subject with a dramatically different SOP phenotype as described with reference to FIGS. 5-7. Similarly to the previous subject, a strong alpha oscillation is exhibited at the beginning of the experiment, that eventually disappeared. In this case, however, the correct responses persisted long after the alpha had diminished [FIG. 8A]. Moreover, there was roughly a 5 minute interval between the time the alpha mode declined and the time the theta and delta power began to increase. This so-called alpha dropout phenotype, having a long interval between alpha power decline and delta/theta power rise, resulted in disagreement between standard sleep scoring and behavioral analysis.

Specifically, in the period between the loss of alpha and loss of response, the hypnogram [FIG. 8D] described the subject as being predominantly in Stage N1, with a brief period of Stage N2, and a short period of Wake when there was a short increase in alpha. Thus a standard interpretation of the hypnogram would place sleep onset at the first epoch of Stage N1, approximately 3 minutes into the SOP. This stands in contrast to the behavioral data of FIG. 8B, which continued to indicate wakefulness for another 5 minutes past the first epoch of Stage N1. The wake probability curve [FIG. 8C], however, integrates all the data such that the estimate of Pr(Wake) was still high during this period, declined slightly, and had a large uncertainty as a result of the contradicting observations. Thus, by combining both the behavioral and physiological data into the estimate of Pr(Wake), the disparity seen between metrics, relying exclusively on either behavior or EEG alone, was bridge. The result is a model that can represent deviation from the population norm as increased uncertainty.

Figure 11A:
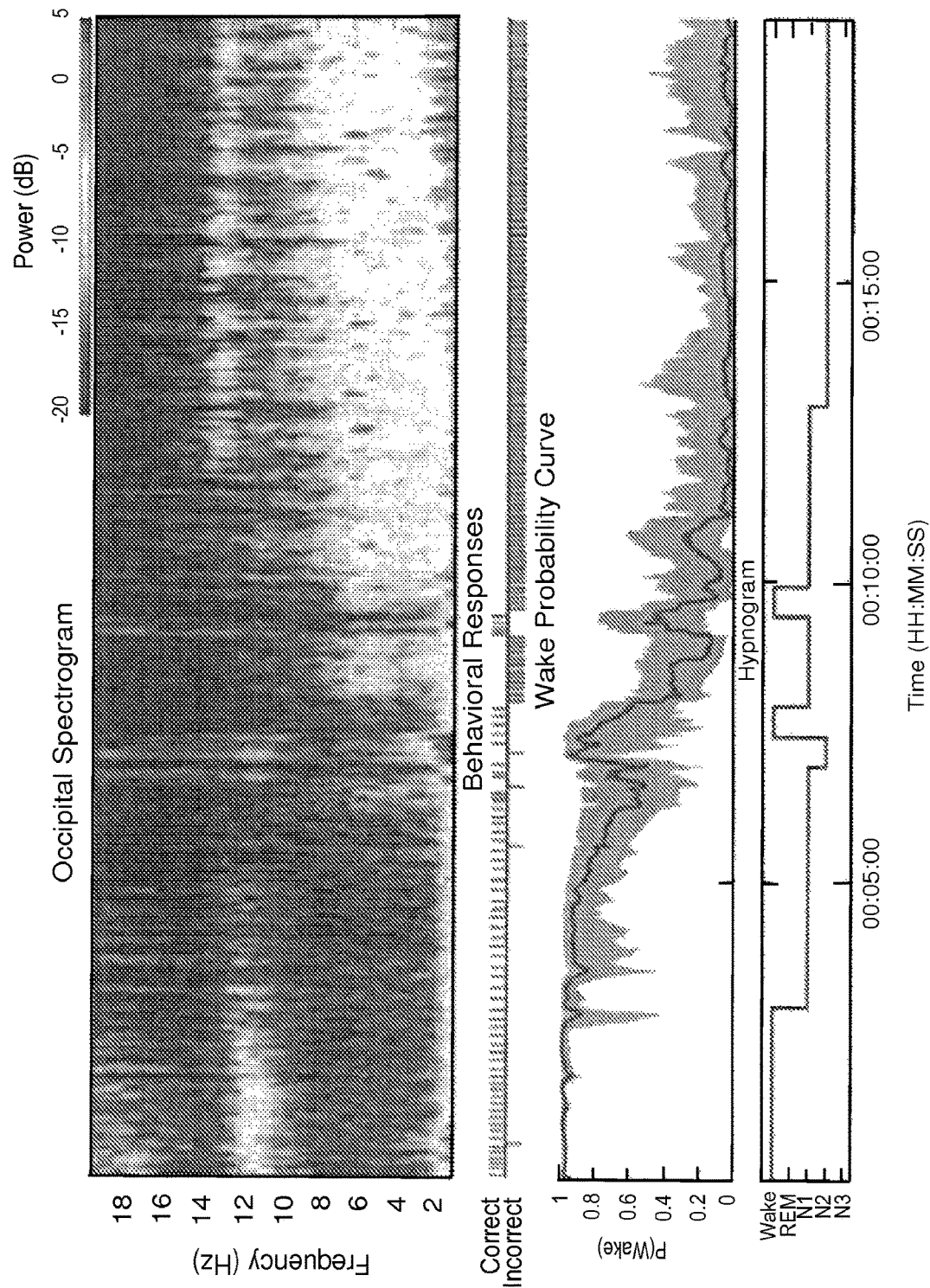
FIG. 11A are graphs showing data obtained from a subject during a first night, wherein the subject exhibits alpha dropout phenotype.
Figure 11B:
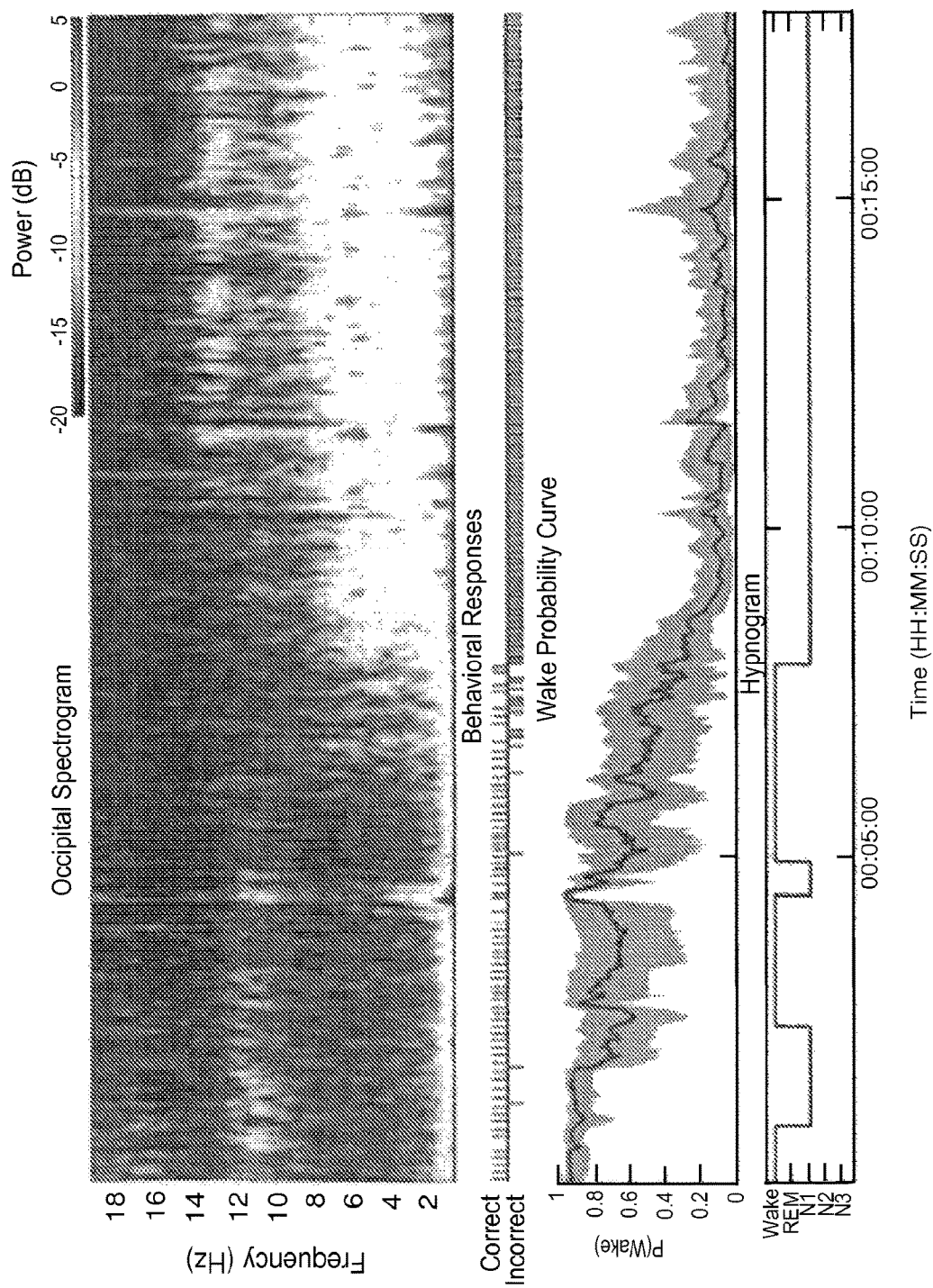
FIG. 11B are graphs showing data obtained from the same subject of FIG. 11A during a second night, exhibiting alpha dropout phenotype.
Figure 12A:
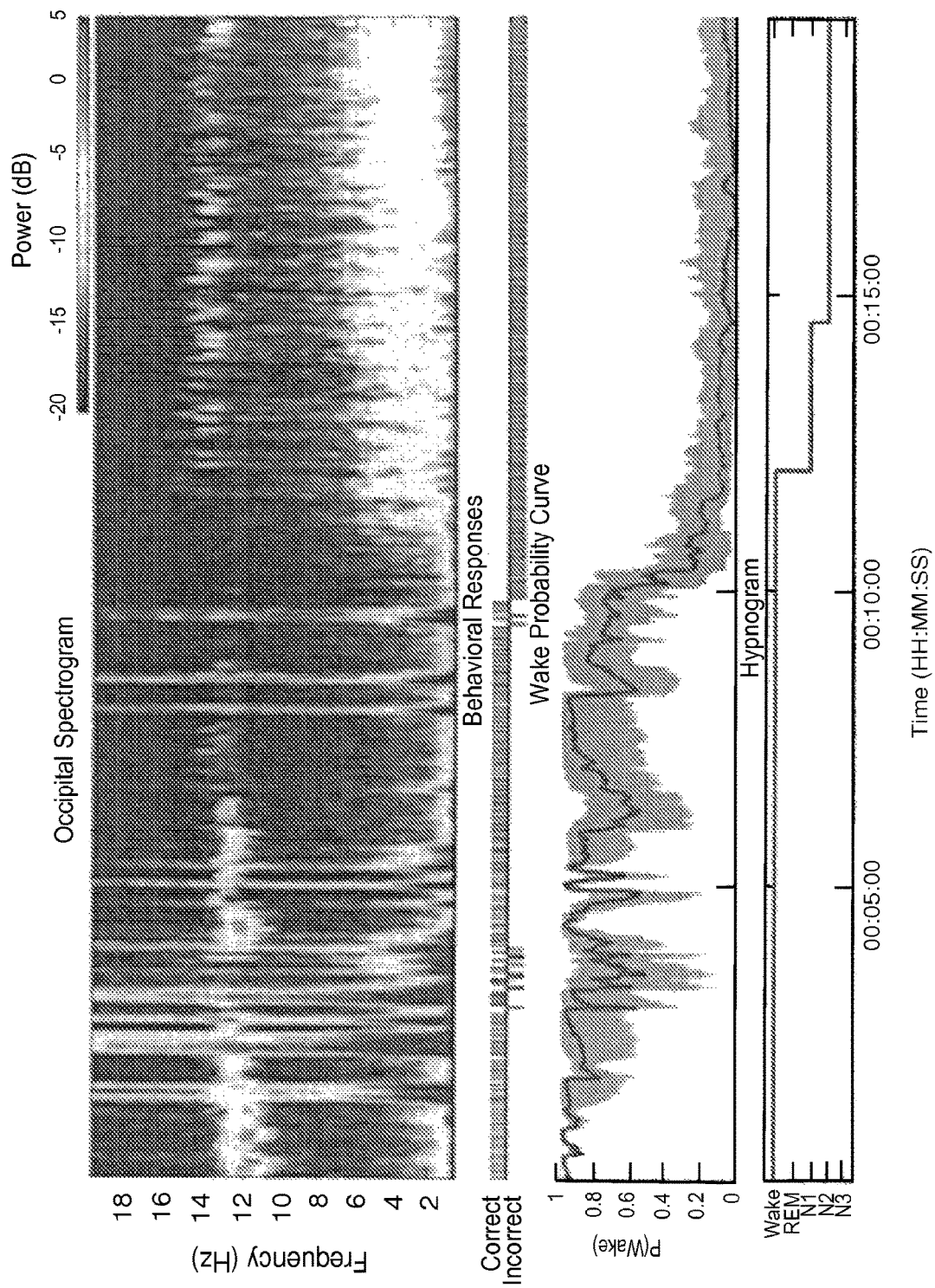
FIG. 12A are graphs showing data obtained from another subject during a first night, wherein the subject exhibits alpha dropout phenotype.
Figure 12B:
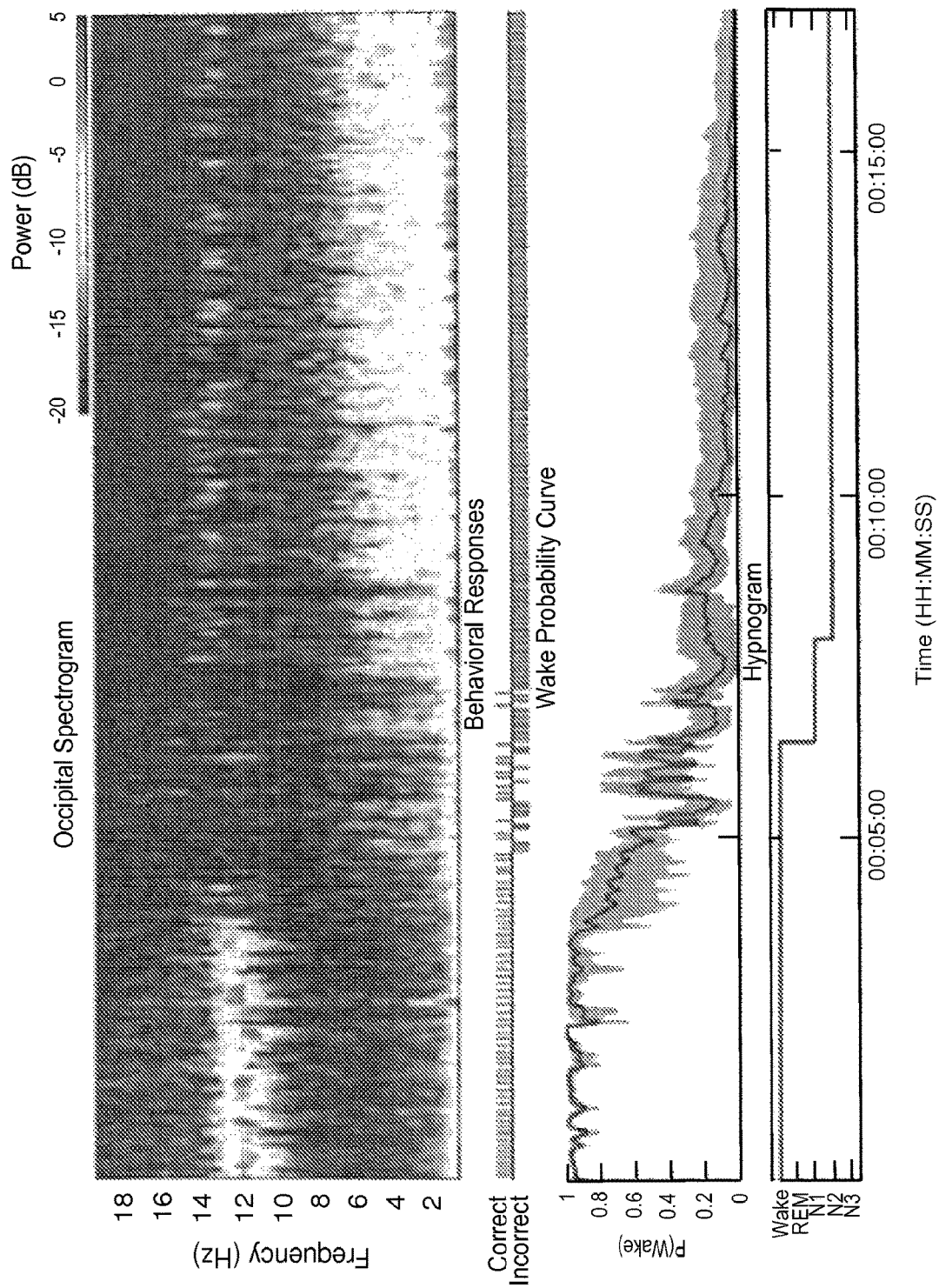
FIG. 12B are graphs showing data obtained from the same subject of FIG. 12A during a second night, exhibiting alpha dropout phenotype.

In the present analysis, 2 of the 9 subjects clearly exhibited the alpha dropout phenotype, with alpha power declined up to several minutes prior to the termination of correct responses and increase of delta/theta power. [shown in FIGS. 11 and 12] For both subjects, this phenotype was present on both experimental nights. Three of the four nights had periods of scored Stage N1 during which there were correct behavioral responses. In none of the cases were correct responses observed in the presence of strong delta and theta. This suggests that loss of alpha power, while necessary, is not sufficient for the loss of behavioral responses.

In clinical practice, the most common definitions for the moment of sleep onset are: the first epoch of Stage N1, the first epoch of Stage N2, the first of any 3 consecutive NREM (N1 or deeper) epochs, and the first of any 10 consecutive epochs of NREM. Though not stated explicitly, any characterization of a point of sleep onset actually imposes a non physiological instantaneous transition model on the SOP. Hence a likelihood analysis was performed to compare how well of the present wake probability model and instantaneous transition models fit the behavioral data. In particular, likelihood is a relative estimate of goodness-of-fit, where given two competing models, the one with the better fit will have a higher likelihood.

Figure 9:
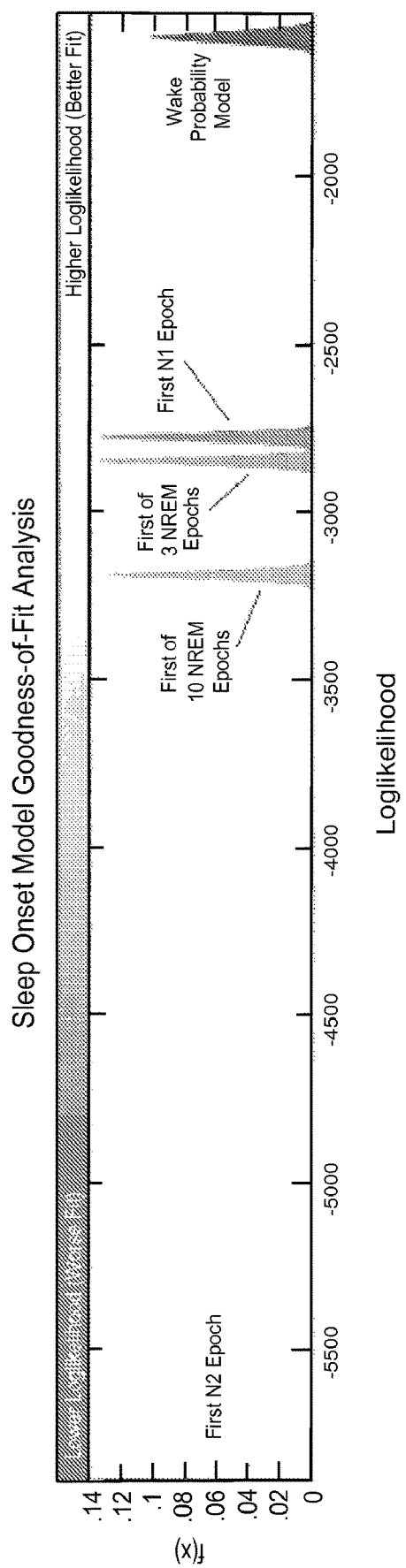
FIG. 9 is a graph depicting a goodness-of-fit analysis of the wake probability model, in accordance with aspects of the present disclosure, versus different instantaneous transition models.

The comparative likelihood analysis showed that the wake probability model, in accordance with descriptions herein, significantly outperformed each of the instantaneous transition models analyzed with at least 99.99% confidence. The results are summarized in FIG. 9 and in Table 1. Overall, the wake probability model fit the data the best, with the largest median log-likelihood (−1589), followed by, in order of goodness-of-fit, the first epoch of N1 model (−2781), the first of 3 NREM model (−2852), the first of 10 NREM model (−3191), and by the first epoch of N2 model (−5828).

TABLE 1

Summary of Bayesian goodness-of-fit analysis for the wake probability model vs. common instantaneous transition models of sleep.

| Model | Goodness-of-fit Rank | Loglikelihood Median | Loglikelihood 95% Credible Interval | Difference Distribution Median | Difference 95% Credible Interval | Credible Interval for Difference > 0 |
|---|---|---|---|---|---|---|
| Wake Probability Model | 1 | −1589 | [−1623 −1556] | | | |
| First N1 Epoch | 2 | −2781 | [−2805 −2757] | 1191 | [1149 1234] | 99.99% |
| First of 3 NREM Epochs | 3 | −2852 | [−2877 −2828] | 1263 | [1211 1306] | 99.99% |
| First of 10 NREM Epochs | 4 | −3191 | [−3217 −3165] | 1630 | [1559 1645] | 99.99% |
| First N2 Epoch | 5 | −5828 | [−5364 −5792] | 4239 | [4189 4288] | 99.99% |

Figure 8E:
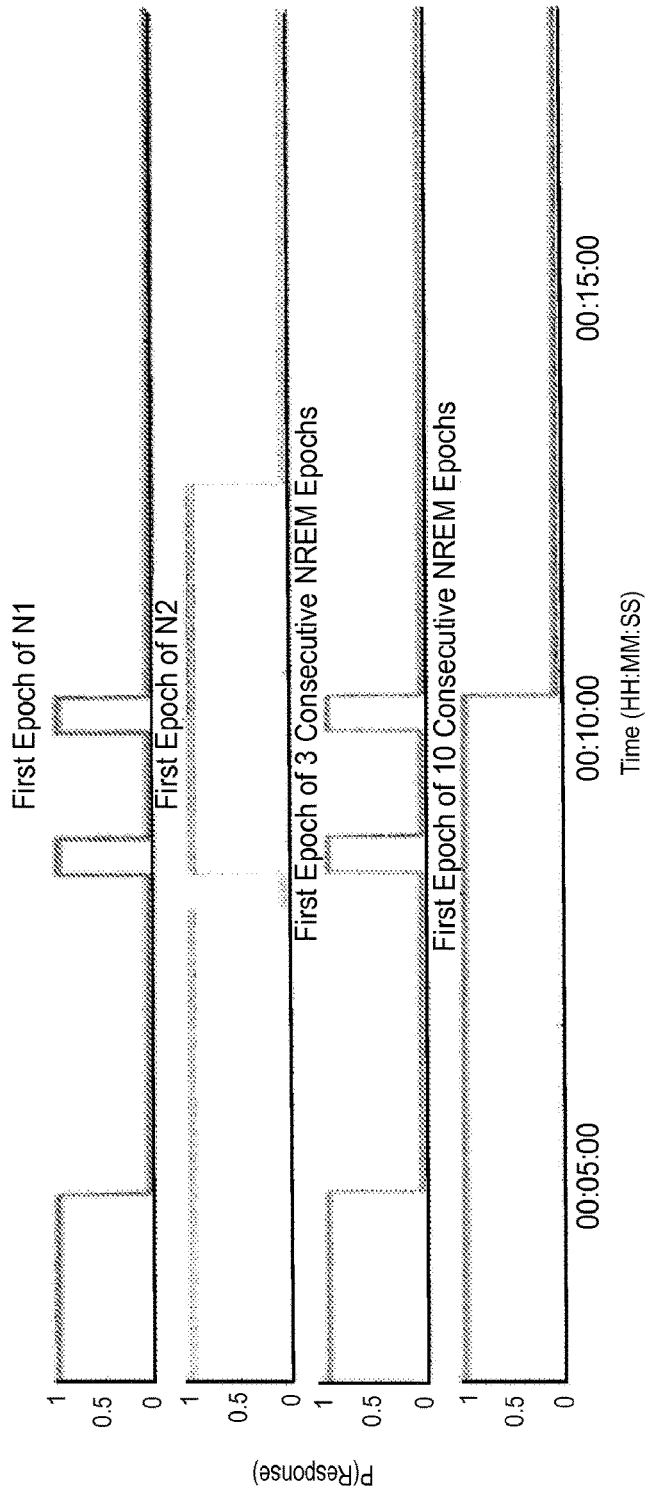
FIG. 8E are graphs showing different instantaneous models associated with the hypnogram of FIG. 8D.
Figure 8F:
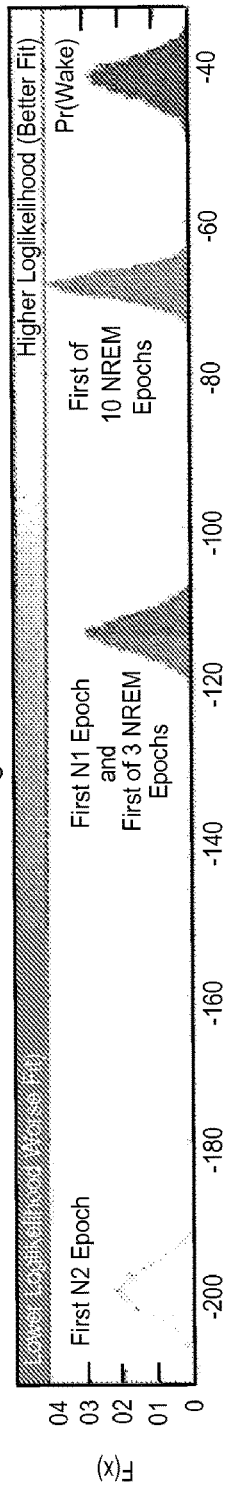
FIG. 8F is a graph depicting results of Bayesian likelihood analysis comparing different instantaneous models with the wake probability approach of the present disclosure.

To illustrate the way in which the wake probability model improves upon the instantaneous transition models, a goodness-of-fit analysis was performed using data from a single night. Specifically, FIGS. 8E and 8F depict the instantaneous transition model response probabilities generated from the hypnogram, and the resultant goodness-of-fit analysis for that experimental session, respectively. This clearly illustrates the way in which the instantaneous transition models implicitly discretize complex dynamics of the SOP into unitary "wake" and "sleep" states, thus losing the ability to capture any nuances in state throughout. Furthermore, since current EEG-based definitions of sleep onset do not include behavioral information, the assumption that Stage N1 is equitable with "sleep" can be misleading, particularly for subjects responding past the alpha dropout.

As shown in FIG. 8F, the wake probability model of FIG. 8C fit the behavioral response data the best, with median log-likelihood of −41, which significantly outperforms the instantaneous transition models with at least 99.99% confidence. Within the class of the instantaneous transition models shown in FIG. 8C, the first of any 10 consecutive NREM epochs model performed the best in this particular case, with a median log-likelihood of −68. In this case, the first epoch of N1 model and first of 3 consecutive NREM epochs model both provided the same response probability estimates, and each had a median log-likelihood of −113. Finally, the first epoch of N2 model performed the worst, with a median log-likelihood of −199.

Overall, the above-described results suggest that the wake probability model is a more mathematically and physiologically appropriate metric with which to track the SOP than are the current hypnogram-based metrics.

A key strength of the wake probability model described herein is that it can characterize EEG activity for groups of subjects across the entire SOP, rather than at a single point of alignment. Using the wake probability curves from multiple subjects, a SOP population spectrogram can be computed, depicting the median cross-subject EEG power spectrum as a function of the behavioral response probability.

Figure 10A:
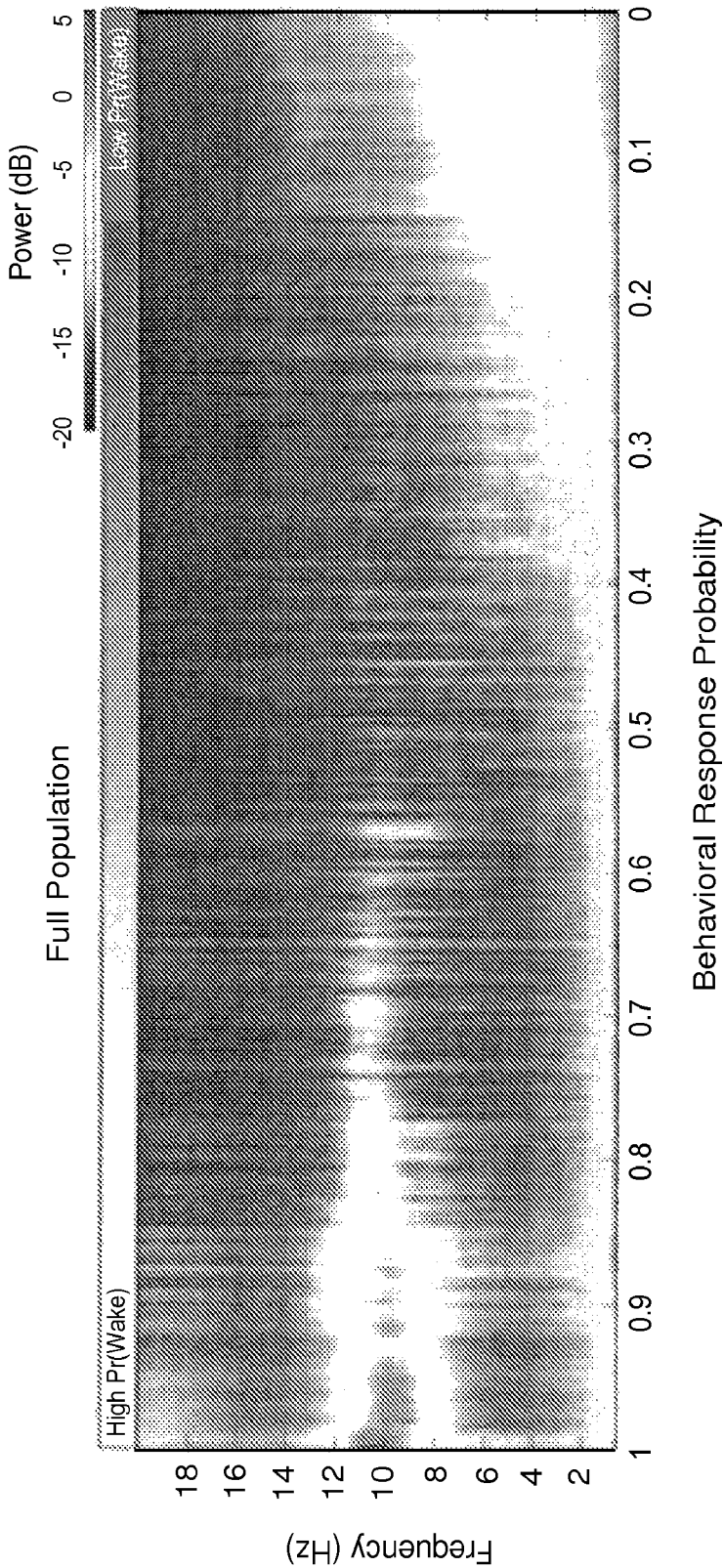
FIG. 10A is an example population spectrogram visualizing EEG power spectra as a function of behavior response probability/wake probability.
Figure 10B:
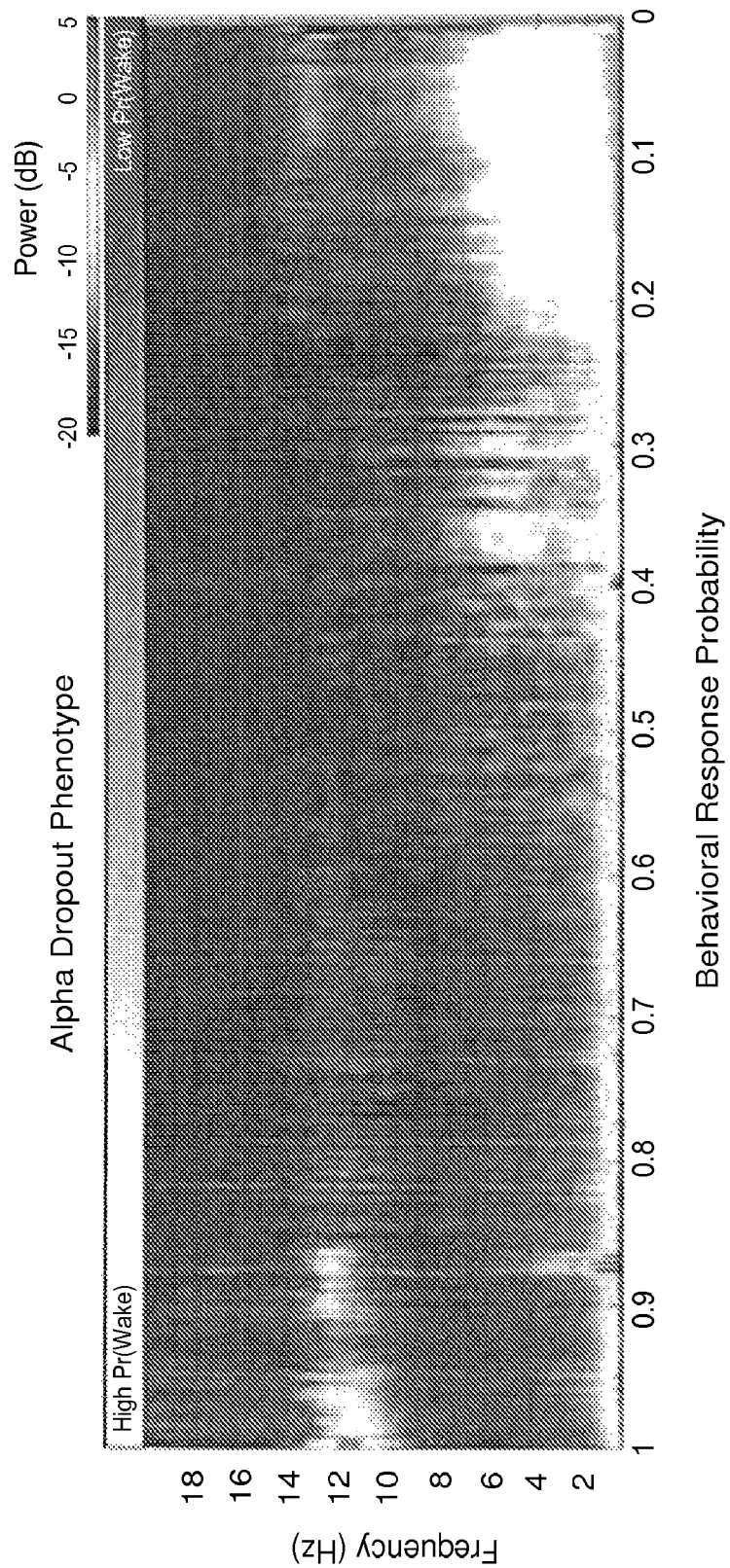
FIG. 10B is an example alpha dropout phenotype spectrogram

Specifically, the SOP population spectrogram was computed using the data from all the subjects and nights [FIG. 10A]. The results clearly show the dynamic transition from a strong alpha mode to increasing delta/theta power as the probability of response progresses from 1 to 0 during the onset of sleep. As shown in FIG. 10, as the SOP progresses, the alpha power reduced in amplitude, dropping out near a response probability of 0.55. The delta/theta mode emerged around a response probability of 0.4, increasing its bandwidth and amplitude as the response probability approached 0.

The SOP population spectrogram can also be used to characterize difference the average EEG activity from different populations at moments at which their behavior is identical. As an illustrative example, an SOP population spectrogram was computed using the data from the two subjects (2 nights/subject, 4 nights total), showing a clear alpha dropout phenotype [FIG. 10B]. The analysis revealed a different spectral structure, with the alpha mode dropping out near a response probability of 0.85, and delta/theta power emerging around a response probability of 0.2.

Figure 10C:
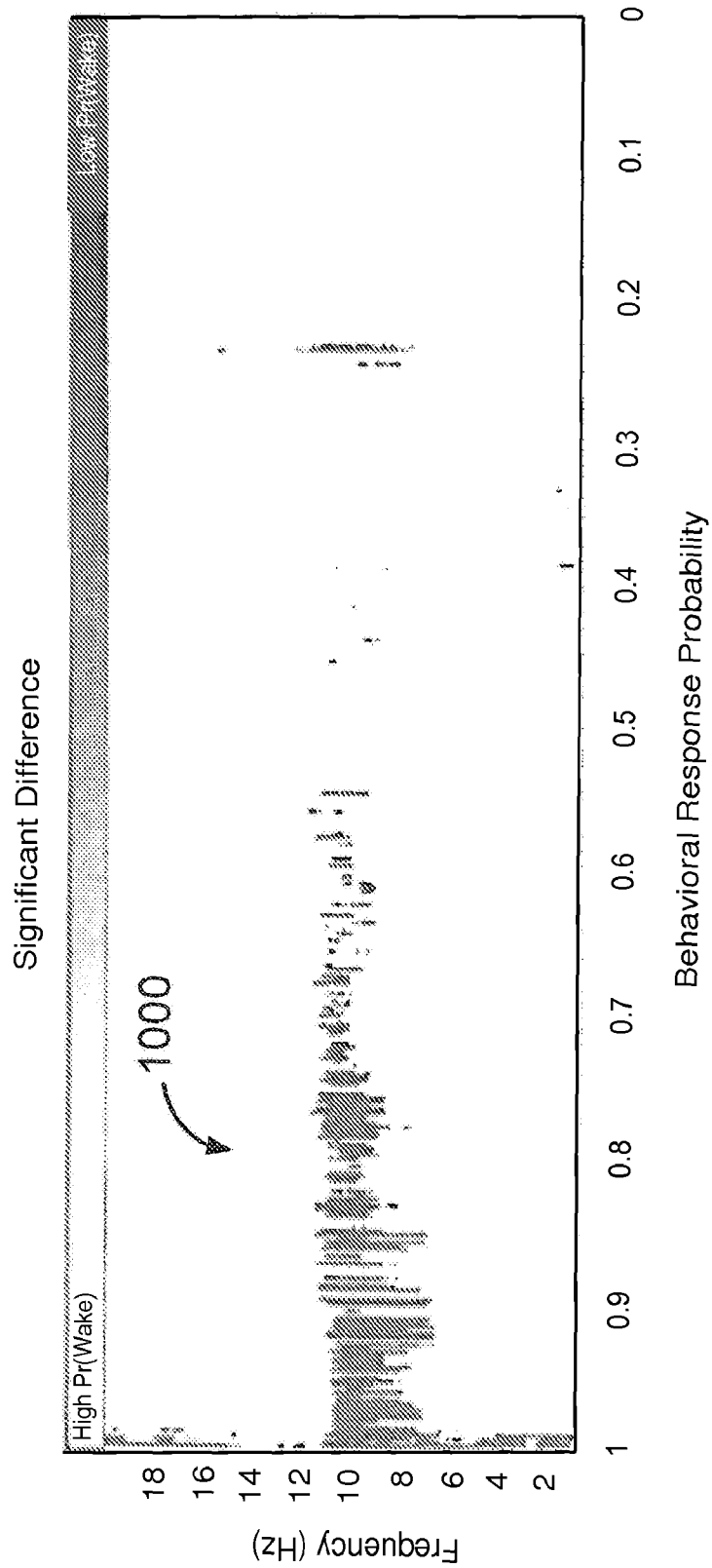
FIG. 10C is an example graph showing time-frequency regions where response probabilities at which two groups differ in spectral power.

A bootstrap procedure was then used to compare the SOP population spectrograms of the subsets of subjects with normal and alpha dropout phenotypes [FIG. 10C]. This analysis revealed a region 1000 of significant difference (95%) covering the bounds of the alpha mode of the standard phenotype. These results suggest that there are indeed subjects that possess significantly reduced alpha power yet can maintain behavior response levels identical to other subjects with a strong alpha oscillation. Analyses such as these therefore provide a principled mathematical framework for characterizing individual SOP phenotypes, as well as for quantifying SOP heterogeneity.

In the present disclosure, a framework for determining a wake probability given evidence from simultaneously observed physiological and behavioral data is developed. This approach improves on contemporary staging of data, where a choice needs to be made between wake and sleep. By contrast, a continuous-valued metric is introduced herein that can track the full spectrum of states during the SOP. In so doing, the SOP can be more accurately characterized as a dynamic system, and can therefore make more precise observations and predictions about the underlying physiology. There are several key factors in this analysis that enable this dynamic, multimodal characterization.

First, the present wake probability model was developed with the goal of tracking the dynamics of a gradually changing SOP, a notion supported by early and more recent scientific studies. However, despite experimental and empirical evidence, SOP dynamics have not been embodied in previous quantitative analyses. By modeling wake probability as a continuous-valued metric, the gap between the evidence and the analysis techniques is bridged.

Second, the model incorporates data from both physiological and behavioral observations. Often, there can disagreement between EEG and behavioral metrics of in the estimation of sleep onset. The main reason for this is that changes in the EEG and behavior are not necessarily time-locked to each other. Experimental observations showed that behavioral responses could persist well into Stage N1—far beyond the point at which many standard criteria for sleep onset would consider sleep—with suggestions that N1 may not be even considered to be true sleep. Additionally, visual scoring paradigms have difficulty handling the heterogeneity observed in the normal EEG population, and consequently will deem a subject to be asleep due to diminished or missing alpha oscillations. It is therefore advantageous to use both behavioral and physiological data in a metric that characterizes the SOP.

Third, the SOP is modeled as a combination of multiple independent components, which can evolve on different time scales. In formulating the model, state equations were defined such that the alpha, delta/theta, and motor states could evolve independently based on the data. This flexibility reflects the idea that interacting systems can activate or deactivate on different timescales throughout the SOP, as observed in intracranial studies of corticothalamic activity. In the present model, it is the superposition of these states that governs the behavioral response data and vice versa. This framework therefore models the SOP as a multifocal, dynamic, neural process, in which each observation type reflects the activity of a systems-level neural component of the SOP, and the aggregate effect of all the systems governs arousal and consequently behavior.

In the present approach, the characterization of the SOP is framed in terms of the probability of wakefulness, rather than the probability of sleep. This is advantageous because the onset of sleep is a complex multifocal process that is constantly evolving. Consequently, estimating a probability of sleep is more difficult, since "sleep onset" could refer to any point on a vast continuum of dynamic neural activity. Hence, choosing to create a model of the waking state and tracking its disappearance is simpler than tackling a complex model of sleep and track its initiation. For instance, Pr(Wake) need not necessarily equal 1−Pr(Sleep), as local sleep-related processes can coexist with wake-related processes in the brain during the SOP. Additionally, the present framework allows the wake probability to be equivalent to probability of a correct response, so that Pr(Wake) can be discussed in terms of behavioral responsiveness, given the additional data from the EEG and EMG.

Historically, defining sleep onset has involved the discretization of sleep via various subjective criteria. The present approach moves away from semantic definitions of a single point of sleep onset, and towards a statistically principled model of SOP dynamics. In the present disclosure, demonstrations regarding sleep characterization of a subject using wake probability, along with how populations can be characterized and compared have been provided. Since the model is Bayesian and computes the full posterior distribution of Pr(Wake), many other rigorous statistical comparisons can be performed for a subject between any set of points in a sleeping period, and also between subjects.

A major advantage provided by the present framework is the ability to make direct comparisons between subjects, for instance, using the SOP population spectrogram. Specifically, in the results described, a subset of subjects were observed to display behavioral responses that persisted for several minutes after loss of alpha power. Since reduced alpha power is one of the key indicators of Stage N1 sleep as defined by R&K scoring, this suggests that such behavior might reflect previous observations of subjects responding to reaction-time tests during Stage N1. Using the SOP population spectrogram analysis, it was demonstrated that, for periods with the same level of behavioral response, these subjects had significantly lower alpha power than the normal phenotype subjects.

A possible mechanism for this particular SOP phenotype could relate to a previous study in which intracranial EEG measurements during the SOP revealed that thalamic circuits tended to change state several minutes before cortical circuits. The latency between changes in thalamic and cortical activity showed substantial variability between subjects. Since it is well known that alpha oscillations are generated when thalamic relay circuits are placed in a depolarized state, the alpha dropout phenotype is consistent with individuals possessing a high latency between changes in thalamic and cortical SOP activity.

Overall, in the SOP alpha power diminishes, and at some time following alpha dropout, there is an increase in delta and theta activity. During this transition period, the rapid tradeoff between the alpha and delta/theta may occur. The latency between the loss of alpha, and the rise of delta/theta, is highly dependent on the individual. Behavioral responses may persist after loss of alpha, but they cease completely in the presence of strong delta/theta power. Therefore, it may be inferred that both the absence of alpha and the presence of delta/theta could be necessary for loss of behavioral response. This conclusion is supported by studies relating high theta power to poor PVT task performance.

Given this scenario, it follows that a subject's individual behavioral and physiological SOP phenotype may likely be due to natural or pathological variation the intrinsic factors governing the sophisticated interplay of multiple thalamo-cortical systems. Hence, the present framework allows for explicitly modeling the dynamics of observations related to this interplay. It may therefore be implemented as a non-invasive tool for the characterization of the state of the systems underlying SOP, as well as for quantifying the factors responsible for various phenotypes.

In summary, the present disclosure describes a system and method that incorporate a statistically-principled, data-driven approach for characterizing the dynamics of sleep. Specifically, a statistical model incorporating behavioral and physiological data into a state-space framework is described. The model can be used to determine a wake probability indicating a degree to which a subject is awake during the sleep onset process.

In this disclosure, particular implementations involving brain and muscular activity measurements along with behavioral observations are described. In particular, in constructing an initial model, specific locations and features of acquired EEG data, namely alpha, delta, and theta frequency band power, were utilized. However, it is clear that such features may not be the only ones present during the SOP, nor are they spatially static. As such, the present framework may be extended to implement more sophisticated models of wakefulness in a straightforward manner. For example, models that incorporate additional physiological observations, such as slow (<1 Hz), beta (15-30 Hz), sigma (12-15 Hz) and gamma (>30 Hz) power, EEG spatial and coherence dynamics, and other biomarkers of sleep, such as body temperature, heart rate, blood pressure, and more, may also be utilized. The models may be augmented to include other behavioral measures.

This flexibility of the present approach provides several major benefits. For instance, by adding more observation modalities, a model may be devised to fully capture current understanding of the multiple neural systems affected during the sleep onset process. In addition, the framework described also allows for adjustments based on new findings. Moreover, since the present framework can be modified to include any or no behavioral task, data previously collected without behavioral information may be retrospectively analyzed using the system and method described.

In some aspects, techniques described herein may be used to characterize phenotypes of different clinical populations, as well as the natural heterogeneity of healthy subjects. By relating model component temporal dynamics to known linkages between observations and their underlying neural systems, the pathophysiology of sleep may be revealed. Additionally, by characterizing the time course of the wake probability curve itself, differences in the rapidity of sleep onset may be quantified in a principled manner. This analysis may be implemented in diagnostic tools for disorders of sleep onset, for instance, comparing a subject's wake probability curve to those from populations possessing a known pathology.

The approach described may also be used to analyze group behavior. For instance, the time course for sets of wake probability curves could also be compared to determine influence factors on the onset of sleep, such as pharmacological agents, pathology, and the first night effect. Furthermore, wake probability could be used to dynamically track drowsiness in situations in which alertness is vital. For instance, the described system and method may be used to detect the point at which wakefulness, and the behavior associated with it, declines.

In addition, the techniques described herein may be used to characterize an individual patient or person's sleep onset dynamics. In some embodiments, this could be used to compare an individual's sleep onset probability curve with those associated with different pathologies, such as insomnia or narcolepsy, for instance, or a healthy population. Reference to normative data from a healthy population could be used to confirm that a patient is healthy, or to identify anomalies in the sleep onset process. Associations with particular pathologies or clinical populations could be used to identify pathology and suggest therapies. In other embodiments, this could be used to track, for an individual, the progression of sleep onset over a period of days, weeks, or months. This could be used to track the effects of an intervention, therapy, medication, or exercise or sleep hygiene procedure, in order to measure the efficacy of such interventions and provide feedback to patients or physicians.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for tracking sleep onset in a subject, the method comprising:
   a) acquiring physiological data using sensors positioned about the subject;
   b) acquiring behavioral data using input provided by the subject;
   c) generating a statistical model of wakefulness by combining information obtained from the acquired physiological data and behavior data;
   d) estimating a probability indicative of a degree to which the subject is awake at each point in time during sleep onset using the statistical model; and
   e) generating a report indicative of sleep onset in the subject, wherein the report tracks and effect of a pharmacological agent on sleep onset of the subject.

2. The method of claim 1, wherein the physiological data is associated with a brain activity, a muscular activity, a respiratory activity, or combinations thereof.

3. The method of claim 1, wherein the method further comprises providing an instruction to the subject to perform a task.

4. The method of claim 1, wherein the method further comprises correlating at least a portion of the acquired physiological data with the behavior data to determine a probability that the behavior data represents a correct response by the subject performing a task.

5. The method of claim 1, wherein the method further comprises computing a confidence interval for the probability at each point in time.

6. The method of claim 1, wherein the method further comprises determining a change in sleep onset using probabilities estimated at step d).

7. The method of claim 1, wherein the method further comprises determining a phenotype of the subject using probabilities estimated at step d).

8. The method of claim 1, wherein the method further comprises computing a population spectrogram using probabilities obtained from multiple subjects.

9. The method of claim 1, wherein the method further comprises determining a sleep condition of the subject by comparing probabilities estimated over a sleep period to those of a population.

10. The method of claim 1, wherein the method further comprises evaluating an effect of at least one drug on the onset of sleep using probabilities computed at step d).

11. The method of claim 1, wherein the method further comprises adapting the statistical model based on an availability of physiological data or behavioral data, or both at each point in time during the sleep onset.

12. The method of claim 1, wherein the method further comprises estimating an instantaneous response probability using the physiological data or behavioral data, or both.

13. The method of claim 1, wherein acquiring physiological data using sensors positioned about the subject comprises acquiring respiratory activity data; and
   wherein the method further comprises:
      providing an instruction to the subject to provide the input timed to the subject's breathing; and
      determining a probability that the subject correctly performed the behavioral action based on a correlation between the respiratory activity data and the behavioral data.

14. The method of claim 1, further comprising:
   estimating a confidence interval of the probability indicative of the degree to which the subject is awake; and
   including the confidence interval in the report indicative of sleep onset.

15. A system for tracking sleep onset in a subject, the system comprising:
   a plurality of sensors configured to acquire physiological data and behavioral data from a subject;
   a processor programmed to at least:
      i) receive the acquired physiological data and behavioral data;
      ii) generate a statistical model of wakefulness by combining information obtained from the received physiological data and behavior data;
      iii) estimate a probability indicative of a degree to which the subject is awake at each point in time during sleep onset using the statistical model;
      iv) generate a report indicative of sleep onset in the subject, wherein the report tracks and effect of a pharmacological agent on sleep onset of the subject; and an output for displaying the report.

16. The system of claim 15, wherein the physiological data is associated with a brain activity, a muscular activity, a respiratory activity, or combinations thereof.

17. The system of claim 15, wherein the output is further configured to provide an instruction to the subject to perform a task.

18. The system of claim 15, wherein the processor is further programmed to correlate at least a portion of the acquired physiological data with the behavior data to determine a probability that the behavior data represents a correct response by of the subject performing a task.

19. The system of claim 15, wherein the processor is further programmed to compute a confidence interval for the probability at each point in time.

20. The system of claim 15, wherein the processor is further programmed to determine a change in sleep onset using probabilities estimated at step iii).

21. The system of claim 15, wherein the processor is further programmed to determine a phenotype of the subject using probabilities estimated at step iii).

22. The system of claim 15, wherein the processor is further programmed to compute a population spectrogram using probabilities obtained from multiple subjects.

23. The system of claim 15, wherein the processor is further programmed to determine a sleep condition of the subject by comparing probabilities estimated over a sleep period to those of a population.

24. The system of claim 15, wherein the processor is further programmed to evaluate an effect of at least one drug on the onset of sleep using probabilities computed at step iii).

25. The system of claim 15, wherein the processor is further programmed to determine an availability of physiological data or behavioral data, or both, from the plurality of sensors.

26. The system of claim 25, wherein the processor is further programmed to adapt the statistical model based on the availability at each point in time during the sleep onset.

27. The system of claim 15, wherein the processor is further programmed to estimate an instantaneous response probability using the physiological data or behavioral data, or both.

* * * * *